(12) United States Patent
Jung et al.

(10) Patent No.: US 12,364,459 B2
(45) Date of Patent: Jul. 22, 2025

(54) ULTRASONIC PROBE AND MANUFACTURING METHOD THEREFOR

(71) Applicant: SAMSUNG MEDISON CO., LTD., Gangwon-do (KR)

(72) Inventors: Jinwoo Jung, Seoul (KR); Jisu Kim, Bucheon-si (KR); Joonghyun Park, Seoul (KR); Sungjae Jun, Hanam-si (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 139 days.

(21) Appl. No.: 17/797,595

(22) PCT Filed: Feb. 5, 2021

(86) PCT No.: PCT/KR2021/001514
§ 371 (c)(1),
(2) Date: Aug. 4, 2022

(87) PCT Pub. No.: WO2021/167274
PCT Pub. Date: Aug. 26, 2021

(65) Prior Publication Data
US 2023/0082716 A1 Mar. 16, 2023

(30) Foreign Application Priority Data
Feb. 18, 2020 (KR) .................. 10-2020-0019455

(51) Int. Cl.
*A61B 8/00* (2006.01)
*G01S 7/52* (2006.01)

(52) U.S. Cl.
CPC .......... *A61B 8/4494* (2013.01); *A61B 8/4444* (2013.01); *G01S 7/5202* (2013.01); *G01S 7/52025* (2013.01); *G01S 7/52079* (2013.01)

(58) Field of Classification Search
CPC .......... A61N 7/00; H01L 27/20; H01L 41/00; G01S 15/8906; G01S 7/52017;
(Continued)

(56) References Cited

U.S. PATENT DOCUMENTS

| | | | | |
|---|---|---|---|---|
| 5,894,646 A | * | 4/1999 | Hanafy | ................ B06B 1/0629 29/25.35 |
| 8,531,178 B2 | * | 9/2013 | Sasaki | .................. B06B 1/0629 29/25.35 |

(Continued)

FOREIGN PATENT DOCUMENTS

| | | |
|---|---|---|
| JP | WO2009/069379 A | 6/2009 |
| JP | 2012-182758 A | 9/2012 |

(Continued)

OTHER PUBLICATIONS

International Search Report dated May 31, 2021 issued in International Patent Application No. PCT/KR2021/001514 (with English translation).

(Continued)

*Primary Examiner* — Jeffrey G Hoekstra
*Assistant Examiner* — Michael Yiming Fang
(74) *Attorney, Agent, or Firm* — Morgan Lewis & Bockius LLP

(57) ABSTRACT

An ultrasonic probe according to one embodiment comprises: a plurality of sound absorbing bodies that form a sound absorbing layer; at least one ground connection part that is joined between the sound absorbing bodies; at least one center connection part that is joined between the sound absorbing bodies and has an electrode; a plurality of side connection parts that are joined between the sound absorbing bodies and disposed outside the center connection part and have an electrode; and a plurality of piezoelectric bodies that are disposed in front of the sound absorbing layer to be
(Continued)

electrically connected to the ground connection part, the center connection part, and the side connection parts.

11 Claims, 17 Drawing Sheets

(58) Field of Classification Search
CPC ............... G01S 7/5202; G01S 7/52025; G01S 7/52079; A61B 8/4494; A61B 8/4444; A61B 8/4488; A61B 8/5207; A61B 2562/12; B06B 1/0629; B06B 1/0677; B06B 2201/76; B06B 1/0215; B06B 1/0662; B06B 1/0607
See application file for complete search history.

(56) References Cited

U.S. PATENT DOCUMENTS

| | | | |
|---|---|---|---|
| 9,073,086 | B2 | 7/2015 | Jung et al. |
| 9,095,879 | B2 | 8/2015 | Jung et al. |
| 2001/0044995 | A1 | 11/2001 | Tezuka |
| 2003/0205947 | A1* | 11/2003 | Klee ..................... G10K 13/00 310/311 |
| 2008/0015443 | A1* | 1/2008 | Hosono ................. B06B 1/0611 600/459 |
| 2009/0062656 | A1* | 3/2009 | Hyuga ................. A61B 8/4488 600/459 |
| 2010/0241004 | A1* | 9/2010 | Jung .................... A61B 8/4444 600/459 |
| 2015/0313574 | A1 | 11/2015 | Jung et al. |
| 2016/0136687 | A1* | 5/2016 | Lewis, Jr. .............. B06B 1/064 29/25.35 |

FOREIGN PATENT DOCUMENTS

| | | |
|---|---|---|
| KR | 10-2010-0104535 A | 9/2010 |
| KR | 10-2013-0078935 A | 7/2013 |
| KR | 10-2014-0134354 A | 11/2014 |
| KR | 10-2015-0041723 A | 4/2015 |

OTHER PUBLICATIONS

Extended European Search Report issued Dec. 7, 2023 for European Patent Application No. 21756457.4.

Supplementary European Search Report issued Jan. 3, 2024 for European Patent Application No. 21756457.4.

Korean Office Action dated Nov. 12, 2024 issued in Korean Patent Application No. 10-2020-0019455 (with English translation).

European Communication dated Mar. 4, 2025 issued in European Patent Application No. 21756457.4.

* cited by examiner

[Fig.1]
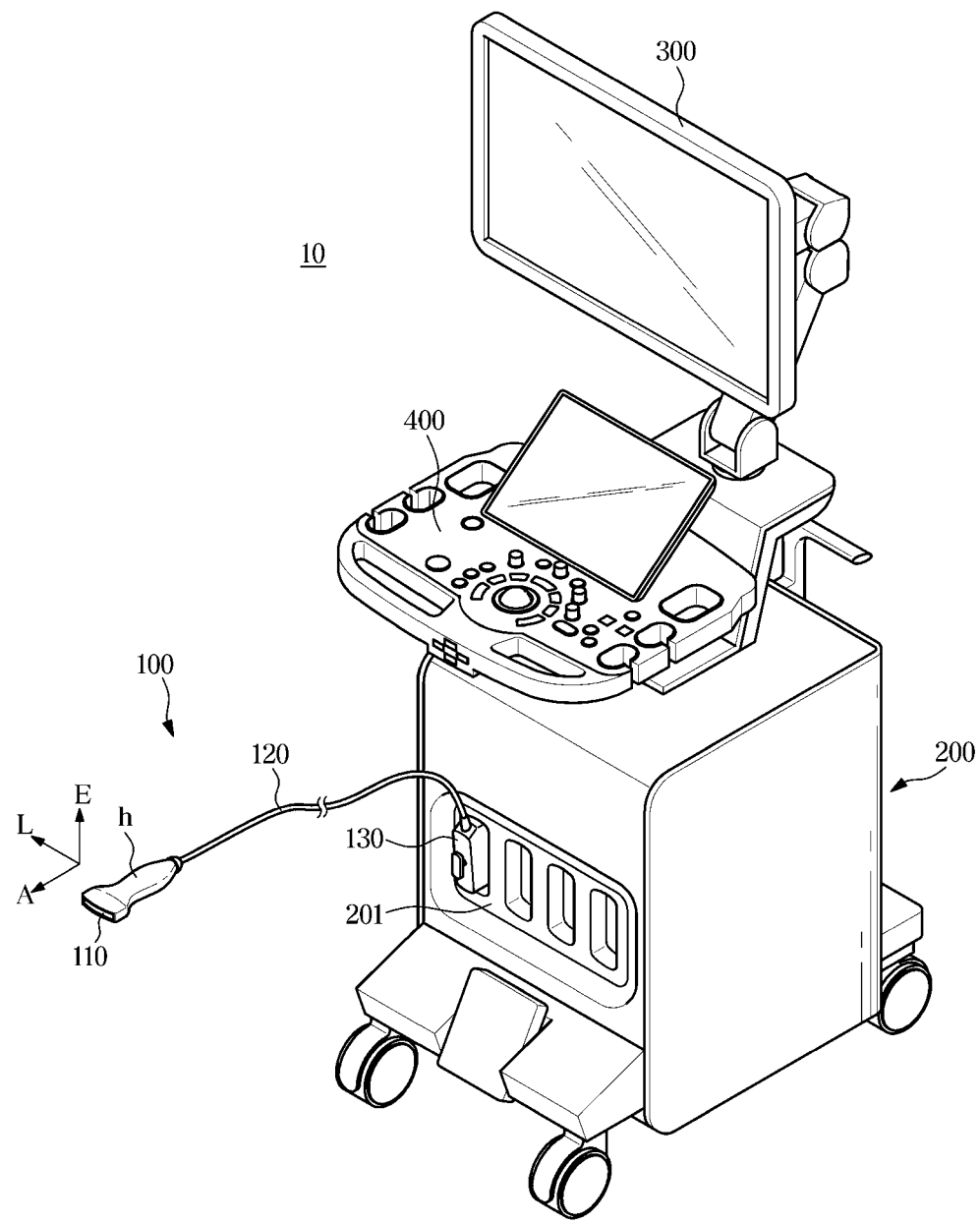

[Fig.2]
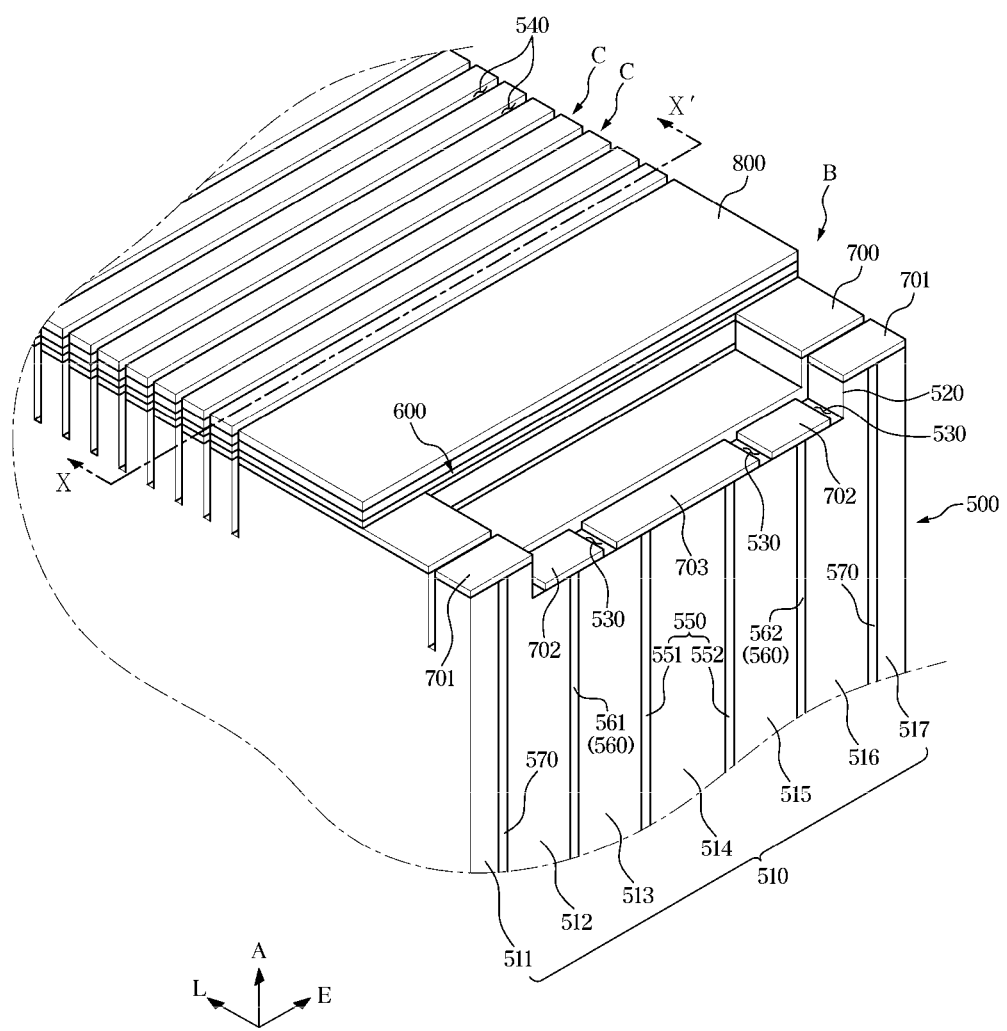

[Fig.3]
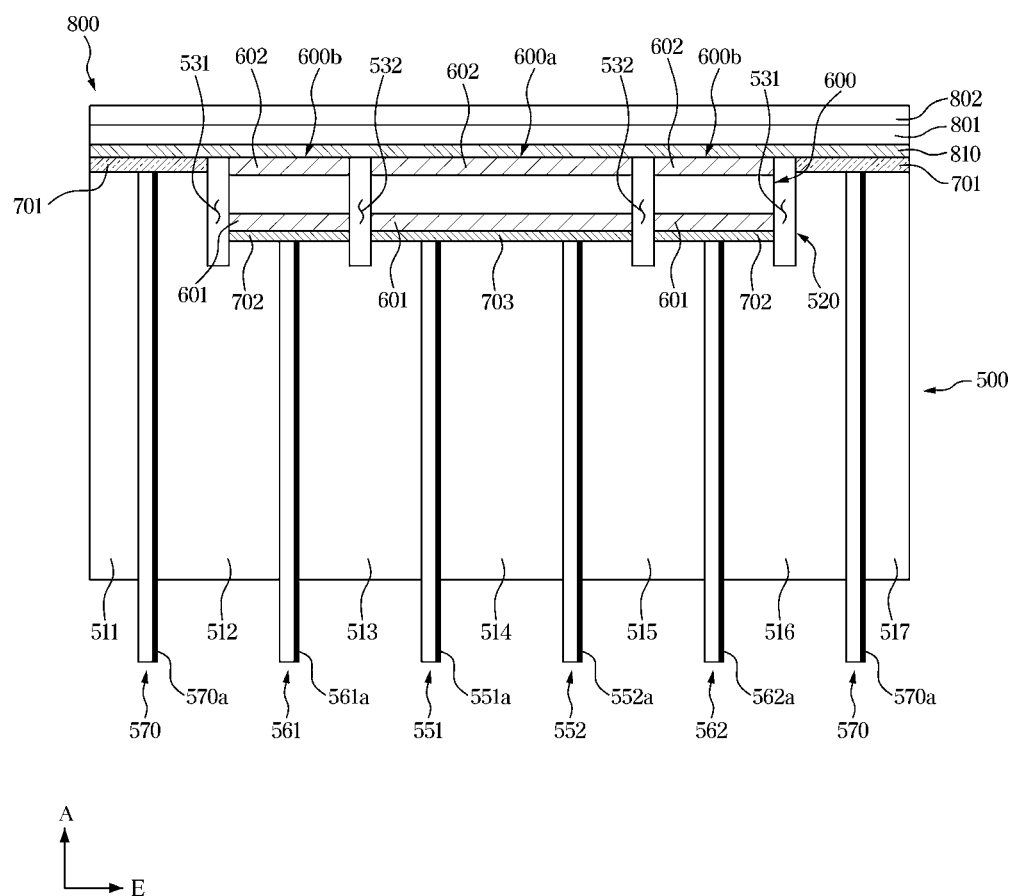

[Fig.4]
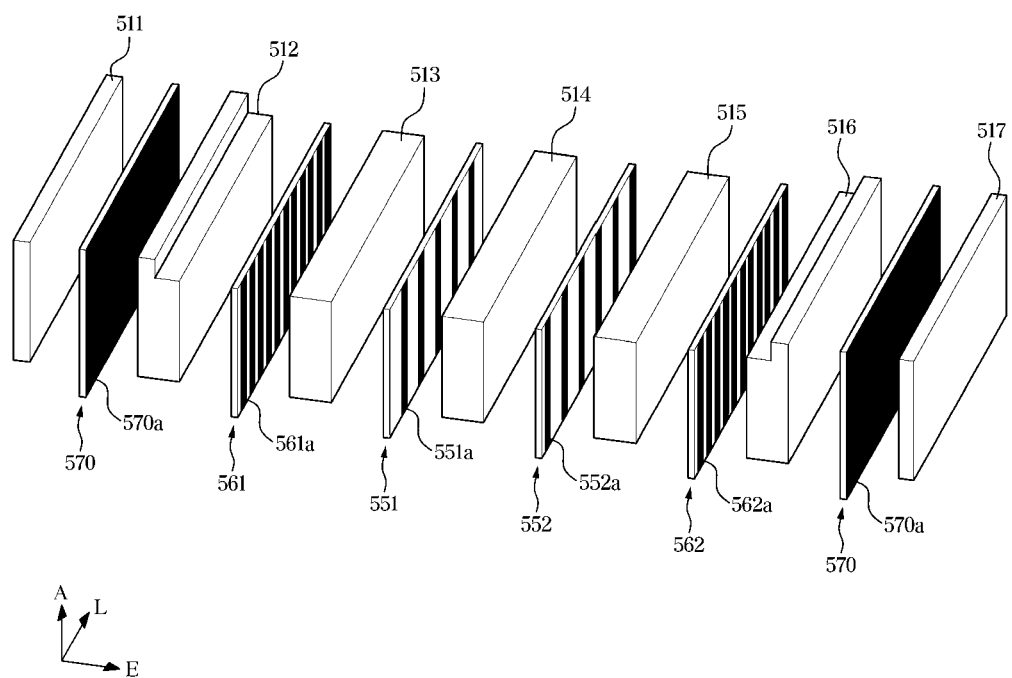

[Fig.5]
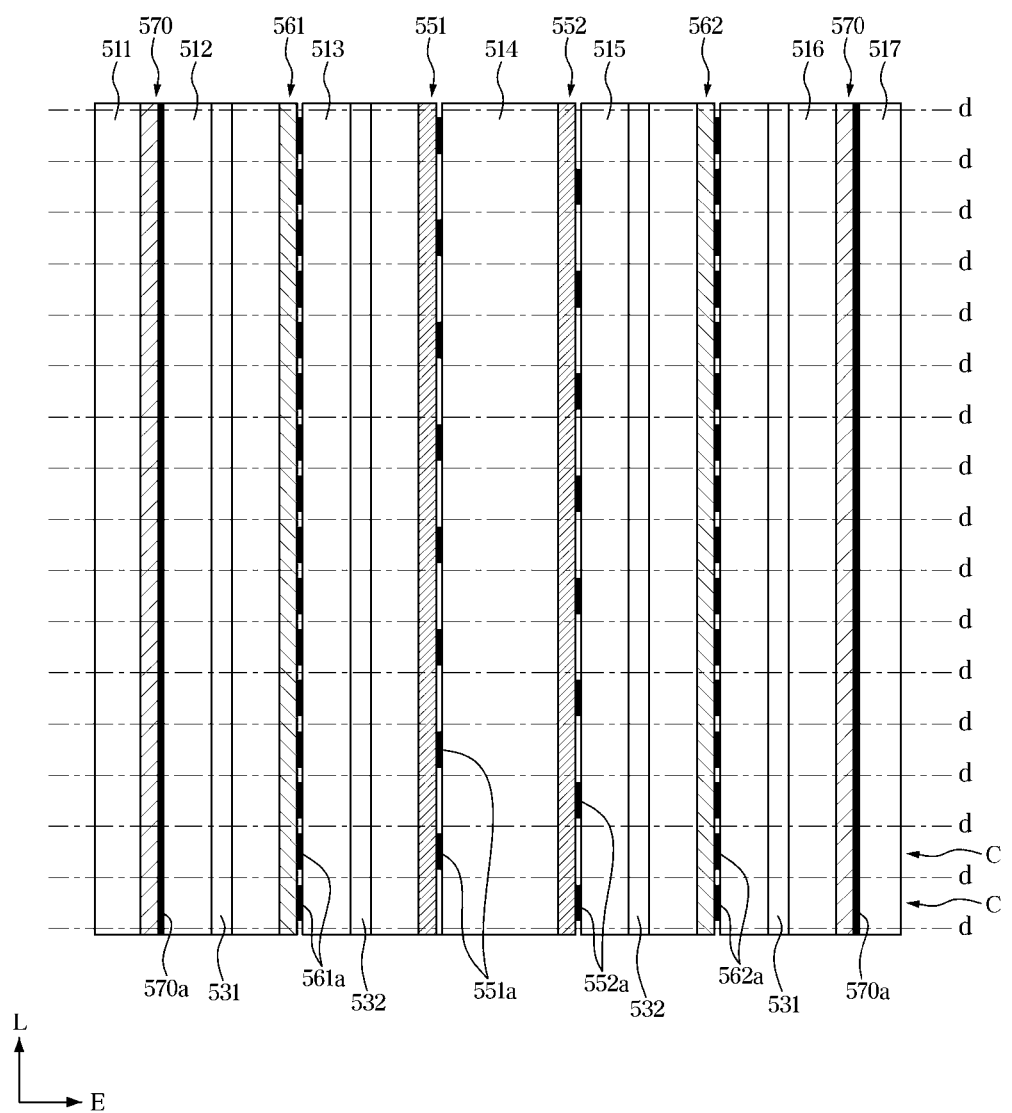

[Fig.6]
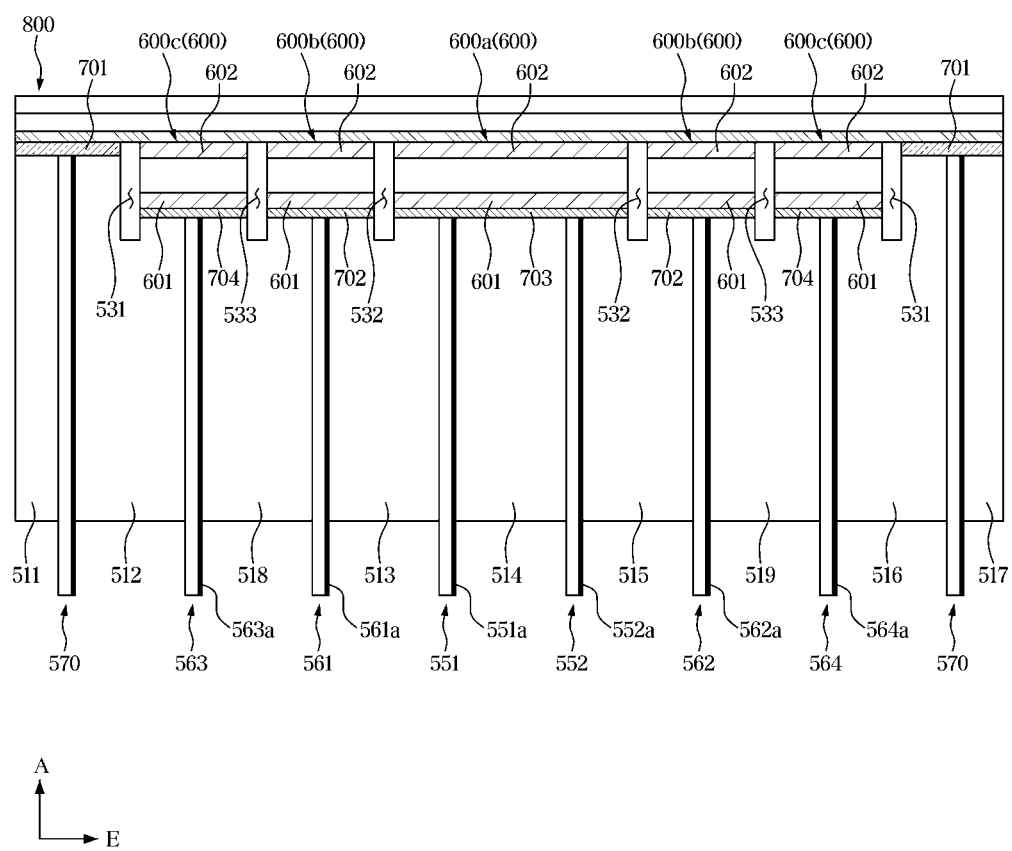

[Fig.7]
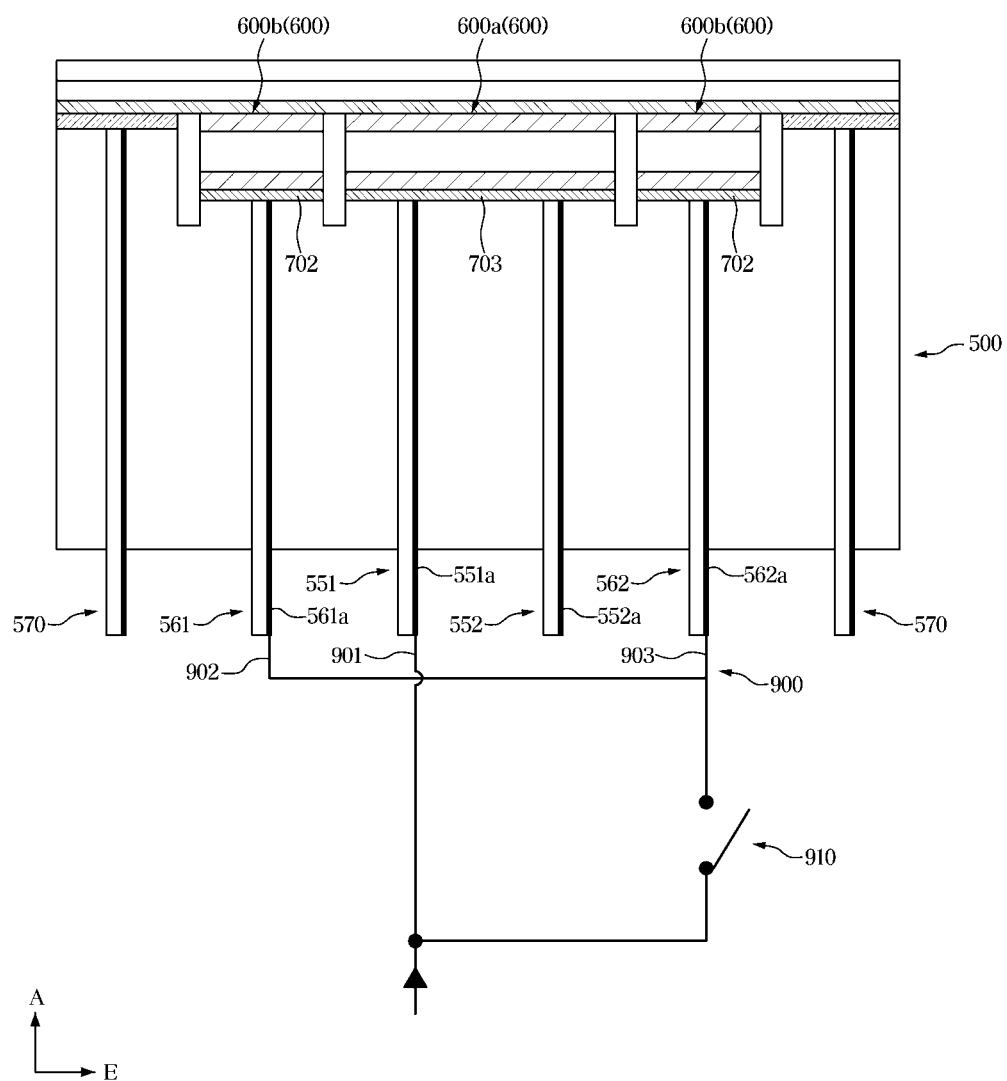

[Fig.8]
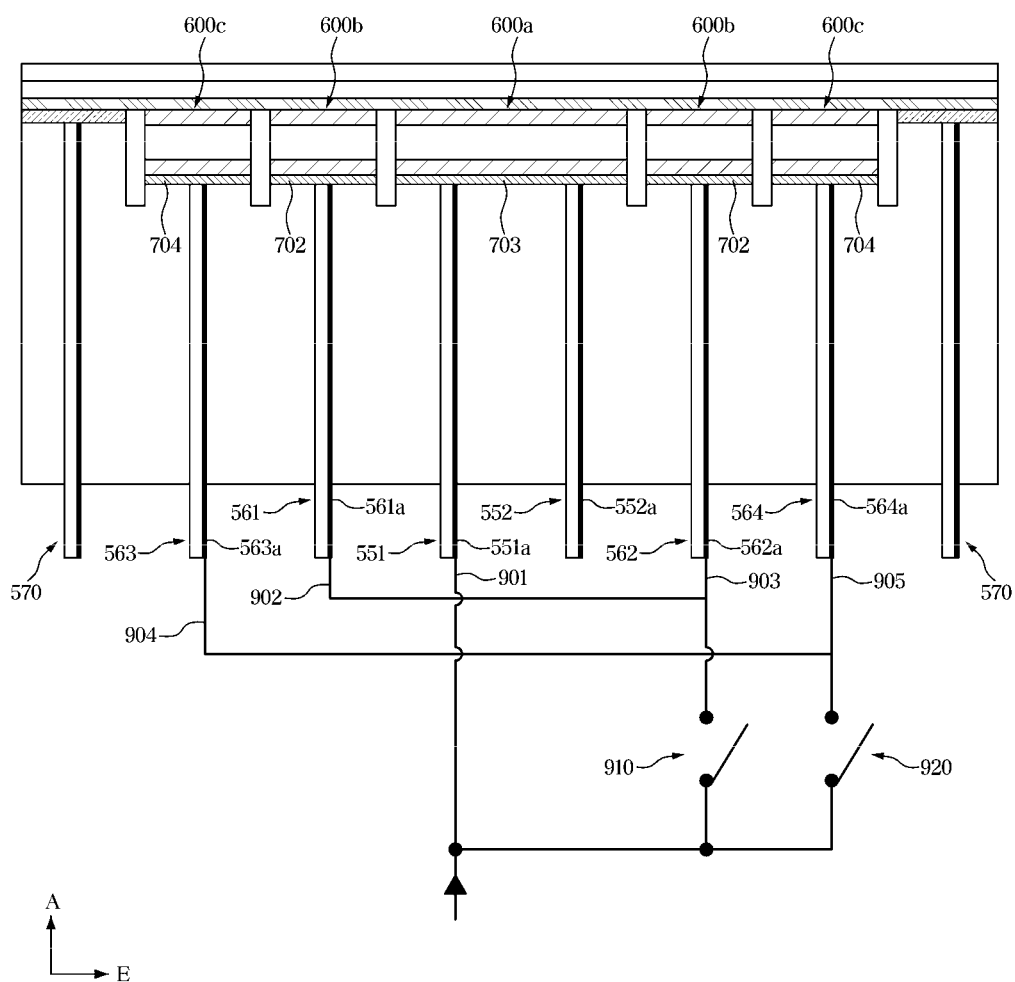

[Fig.9]
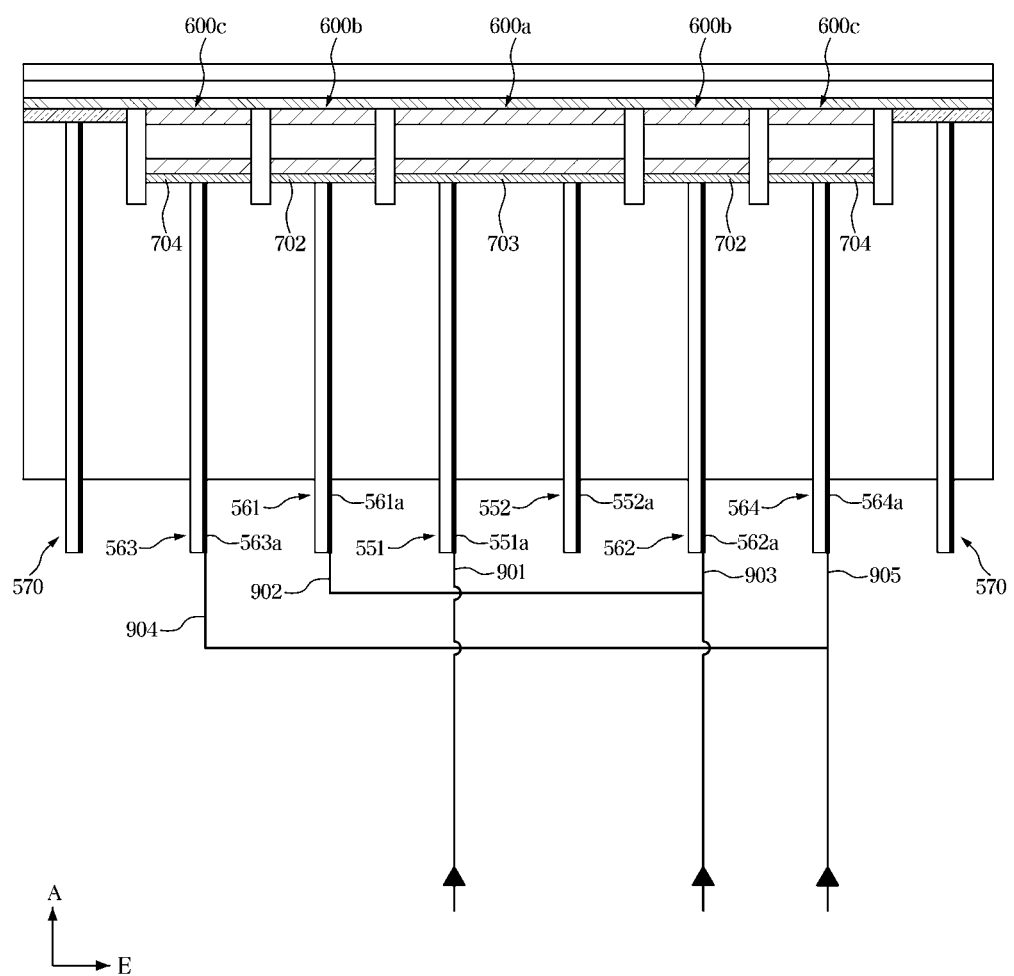

[Fig.10]
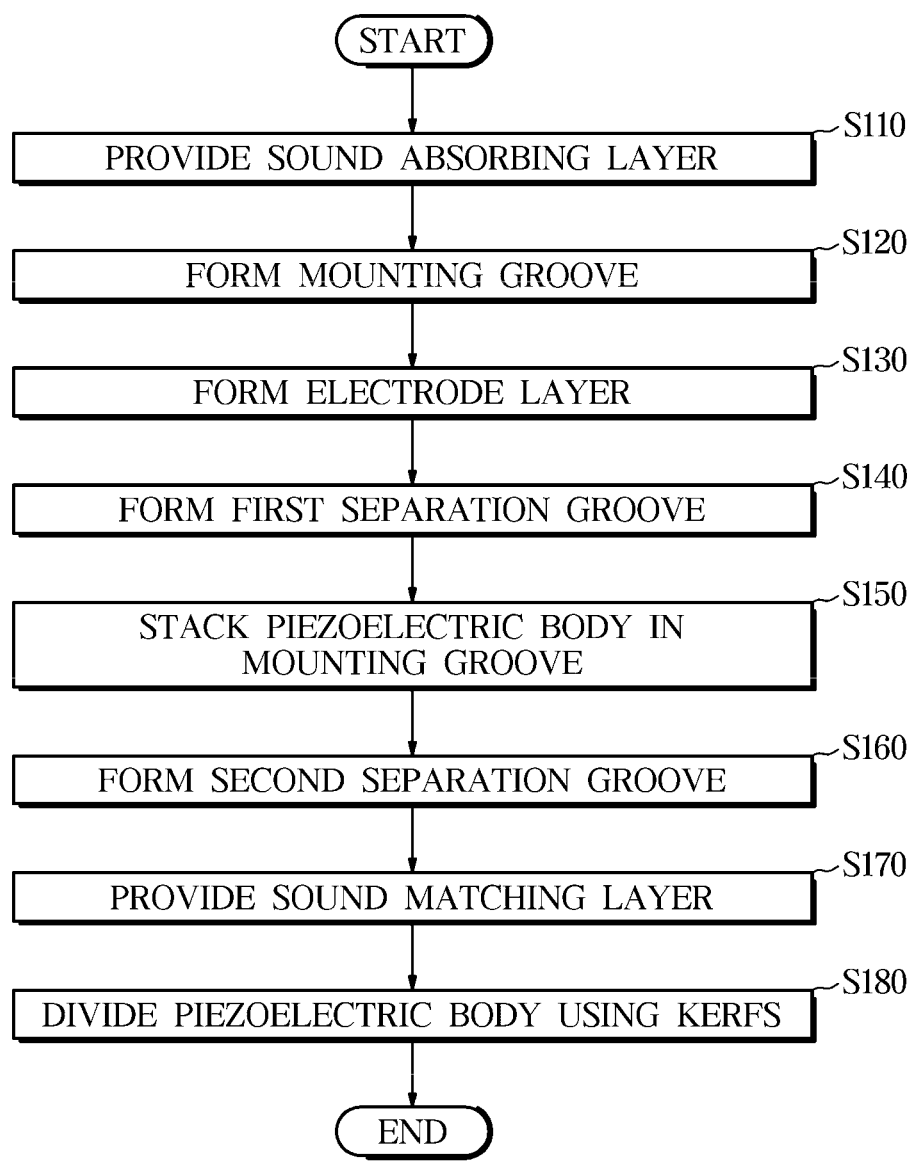

[Fig.11]
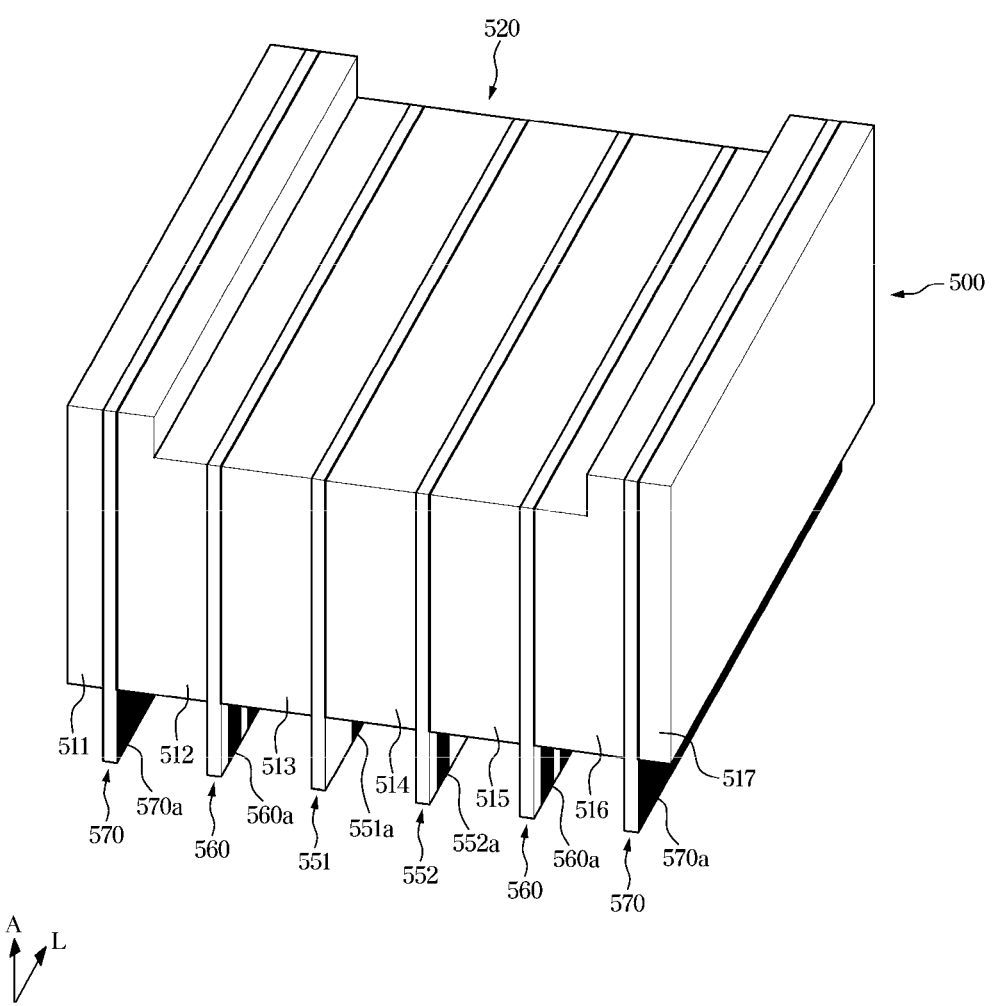

[Fig.12]
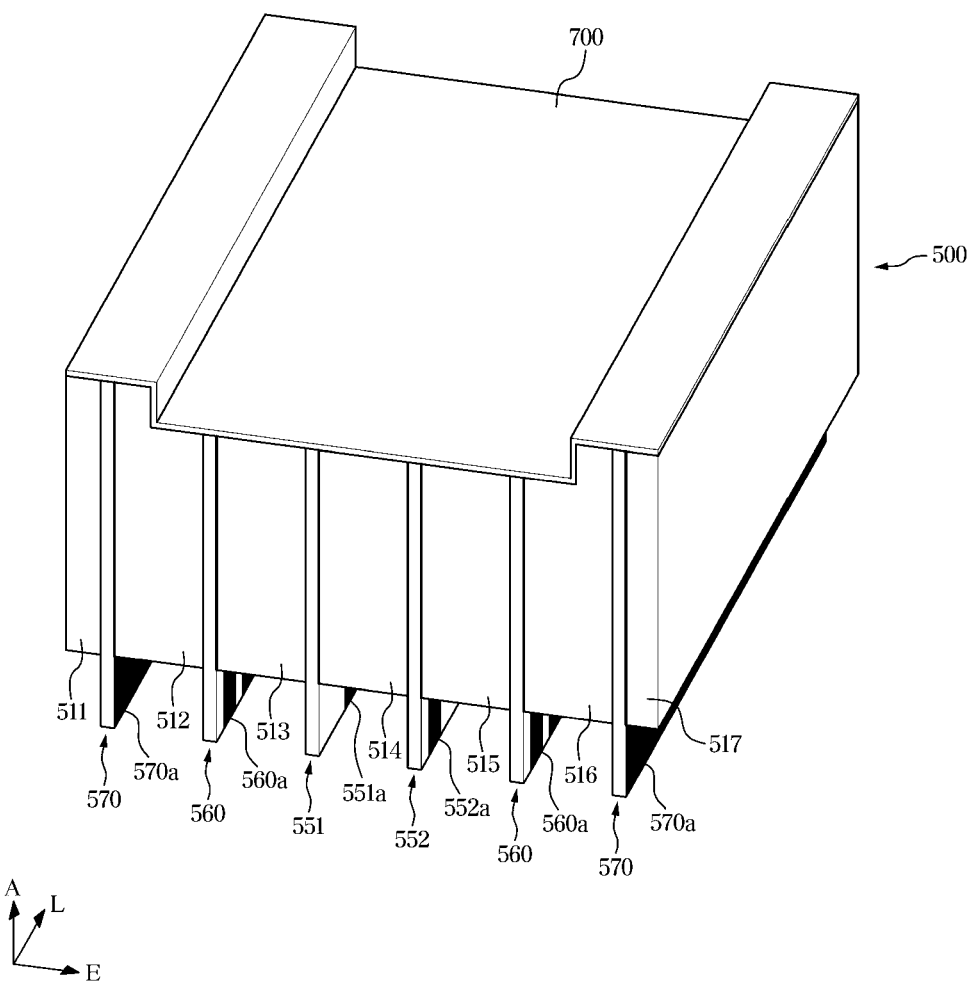

[Fig.13]
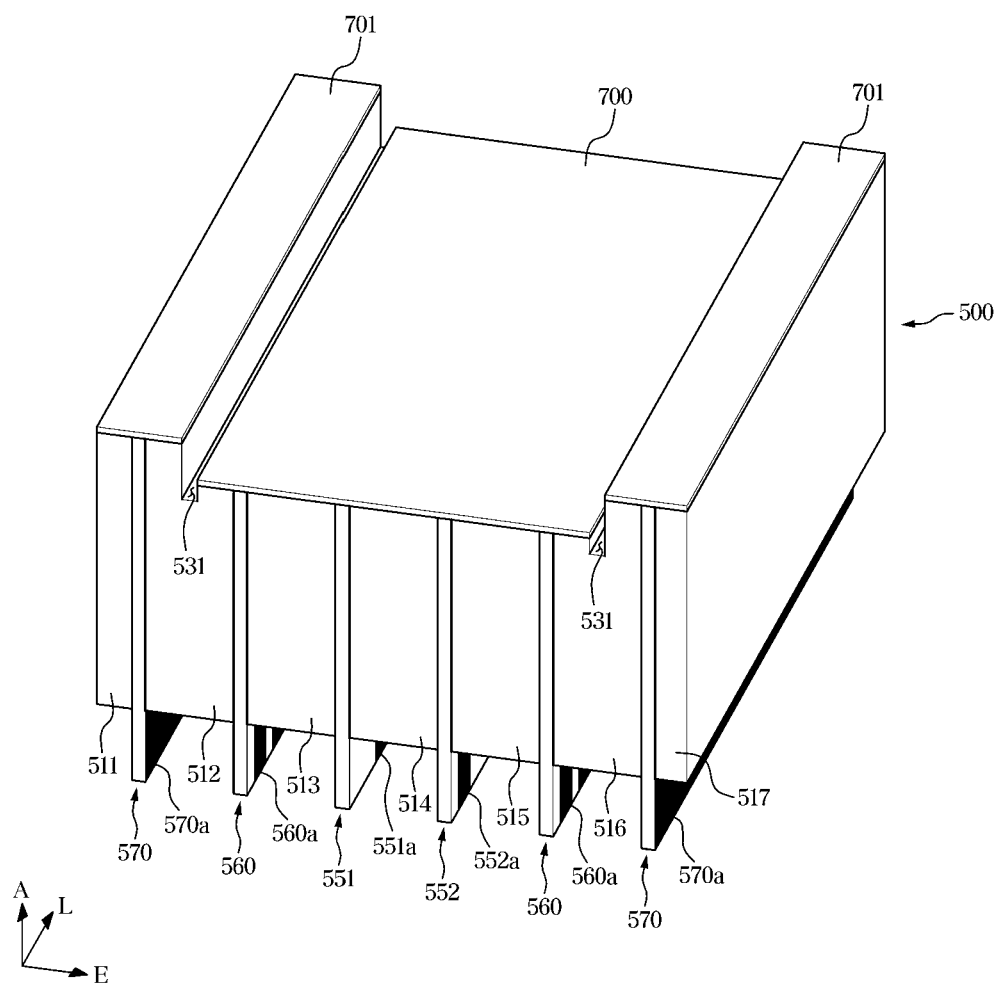

[Fig.14]
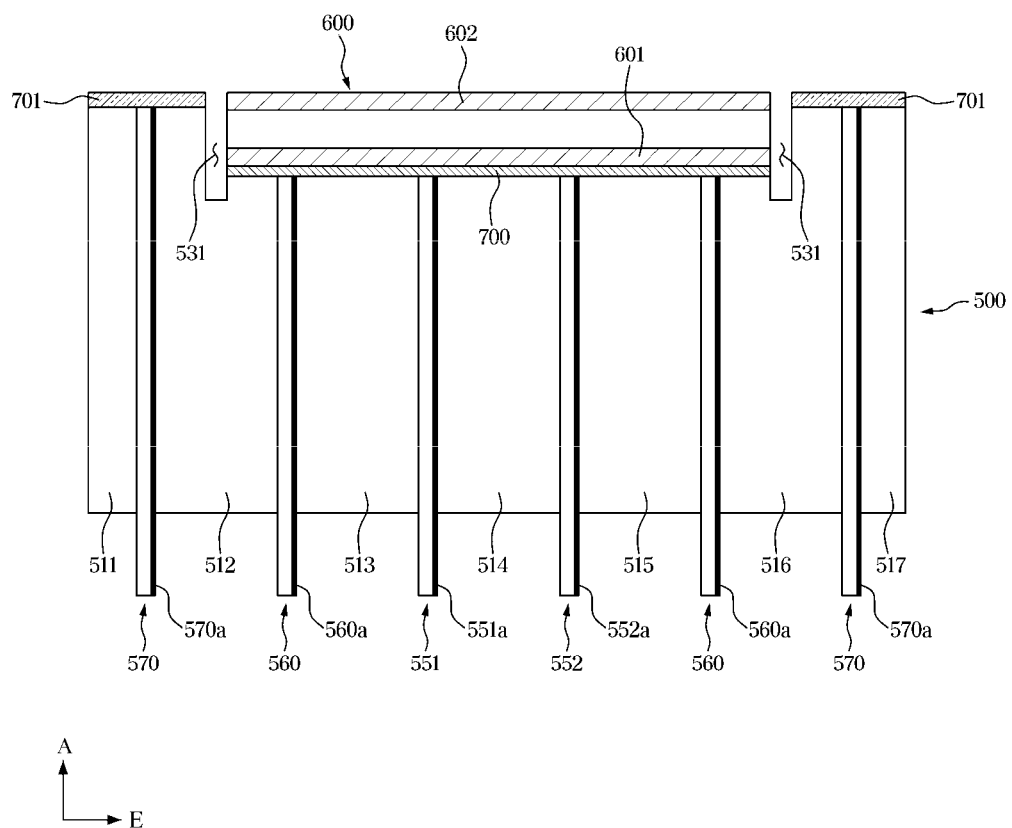

[Fig.15]
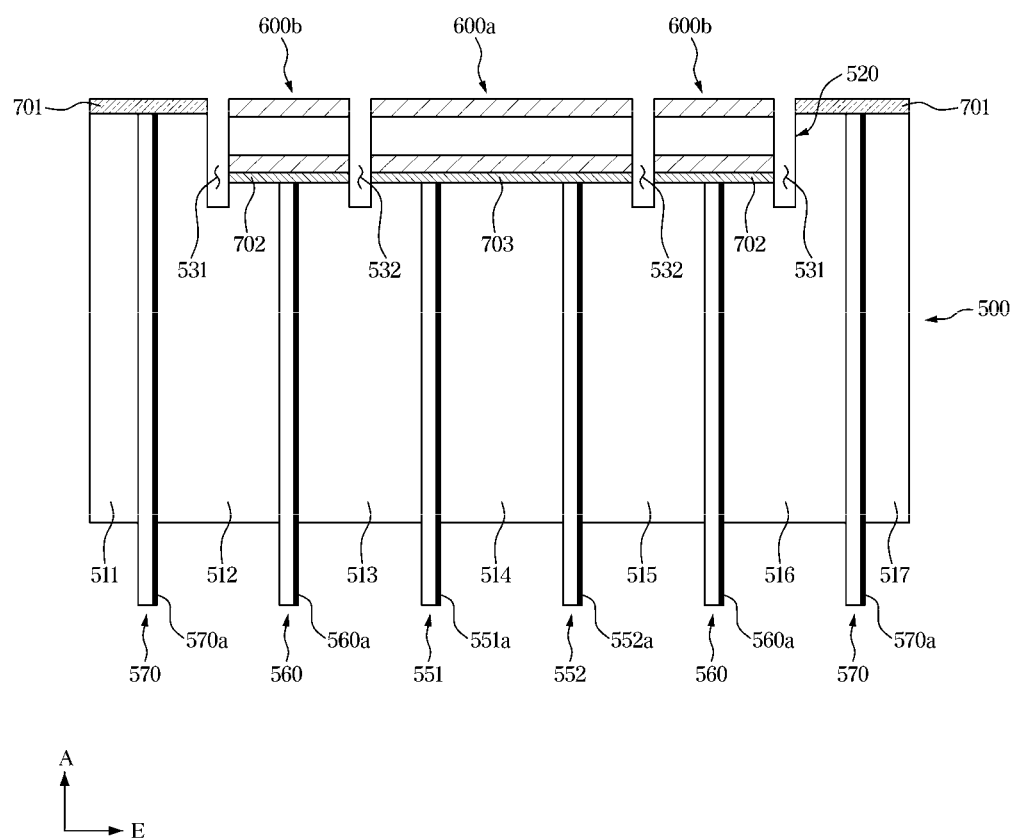

[Fig.16]
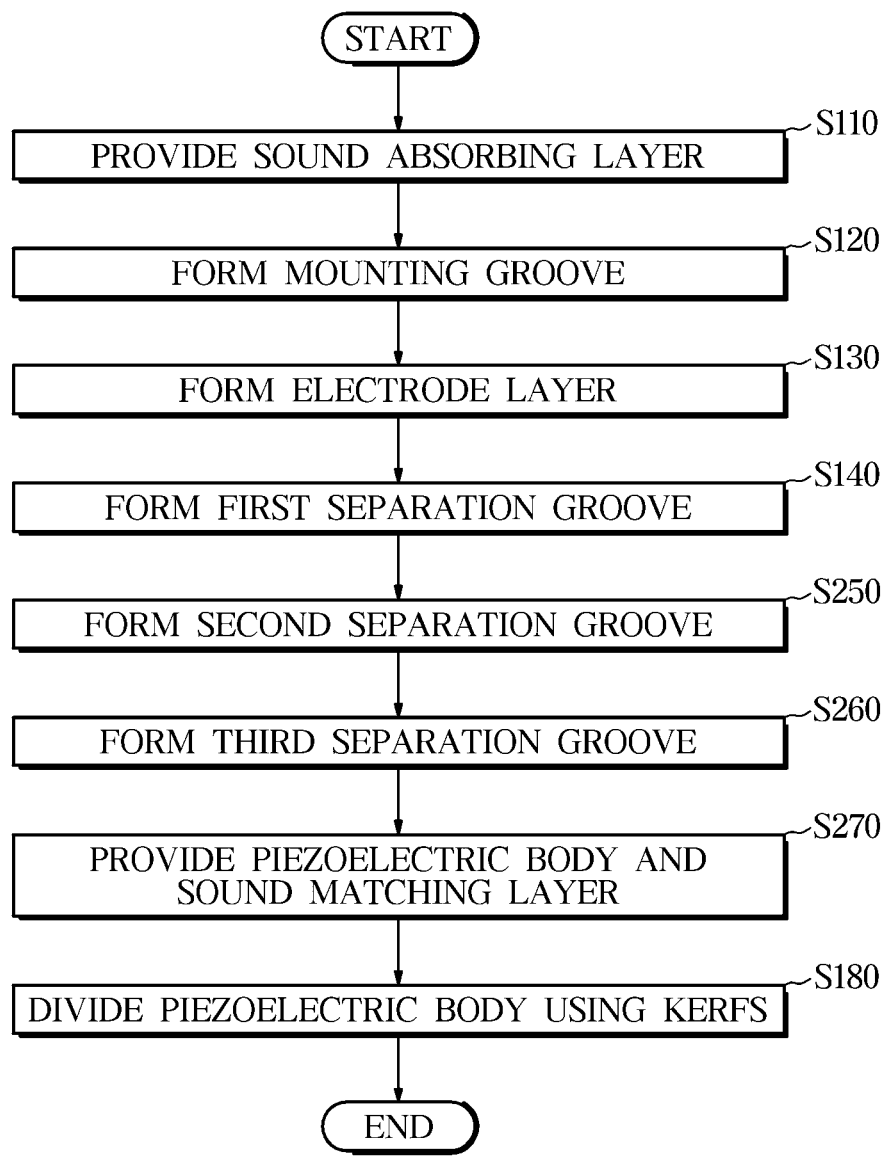

[Fig.17]
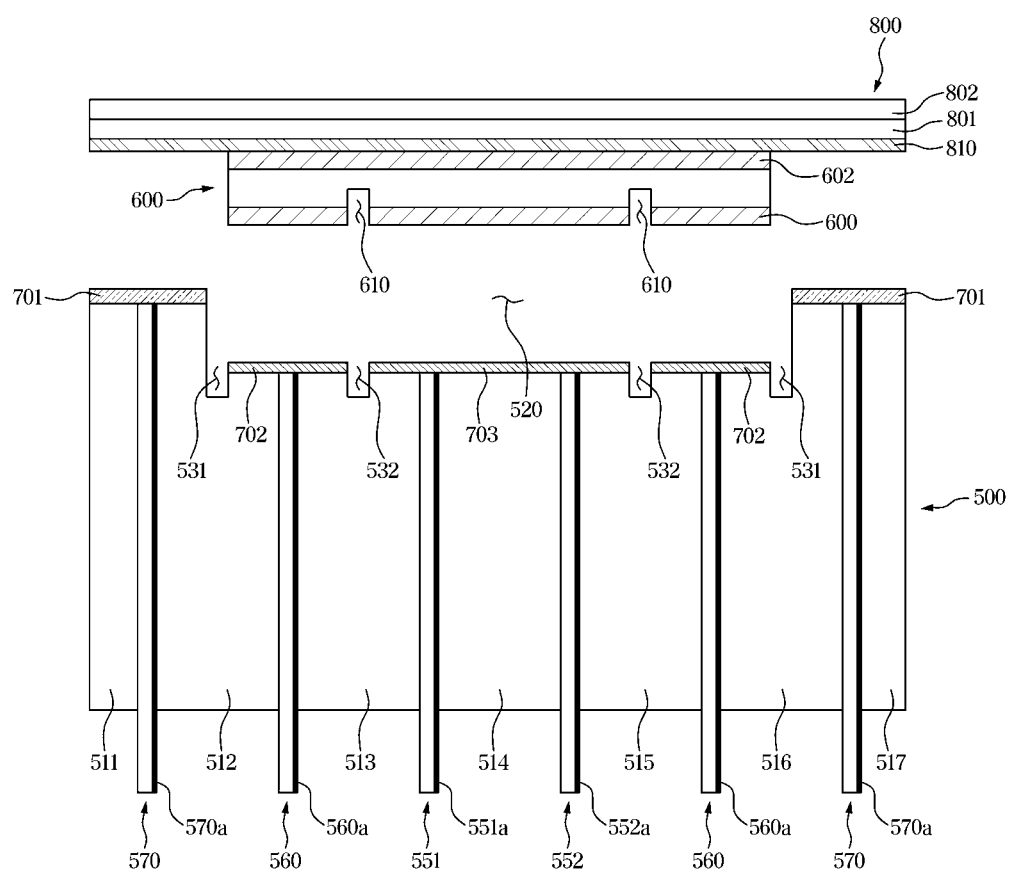

ULTRASONIC PROBE AND MANUFACTURING METHOD THEREFOR

CROSS-REFERENCE OF RELATED APPLICATIONS

This application is the U.S. National Phase under 35 U.S.C. § 371 of International Patent Application No. PCT/KR2021/001514, filed on Feb. 5, 2021, which in turn claims the benefit of Korean Application No. 10-2020-0019455, filed on Feb. 18, 2020, the entire disclosures of which applications are incorporated by reference herein.

TECHNICAL FIELD

Provided is an ultrasonic probe for generating an image of the inside of a subject using ultrasonic waves, and more particularly, to a multi-row ultrasonic probe and a manufacturing method thereof.

BACKGROUND ART

An ultrasonic image device is a device that emits an ultrasonic signal toward a target region in the body of a subject from a surface of the subject and obtains a tomographic image of a soft tissue or an image of a blood flow in a noninvasive manner using information of a reflected ultrasonic signal (an ultrasonic echo signal).

An ultrasonic imaging device is compact, inexpensive, capable of displaying images in real time, and free from radiation exposure, thus securing safety when compared to other types of diagnostic imaging devices, such as an X-ray diagnostic device, an X-ray computerized tomography (CT) scanner, a magnetic resonance imaging (MRI) device, and a nuclear medicine diagnosis device, and therefore has been widely used to diagnose heart diseases, abdominal diseases, urinary organ diseases, and obstetric and gynecological diseases.

An ultrasonic imaging device includes an ultrasonic probe for transmitting an ultrasonic signal to a subject and receiving an ultrasonic echo signal reflected from the subject to obtain an ultrasonic image of the subject, and a main body for generating an image of the inside of the subject using the ultrasonic echo signal received from the ultrasonic probe.

A single-row (1D) probe of the related art is limited in a focal range due to a focal point physically fixed according to a curvature of a lens.

A multi-row probe improved to solve the problem of the 1D probe is capable of controlling a focal region physically or electrically and thus obtaining a high-resolution image in a wider area. Accordingly, in recent years, a multi-row probe of 1.25D (three rows) or more has replaced the 1D (1-row) probe.

DISCLOSURE

Technical Problem

An aspect of the present disclosure provides an ultrasonic probe that includes a plurality of piezoelectric bodies in columns in an elevation direction, and a manufacturing method thereof.

An aspect of the present disclosure provides an ultrasonic probe that is easy to manufacture and has a structure for preventing degradation in performance.

An ultrasonic probe according to an aspect of the present disclosure includes a plurality of sound absorbing bodies configured to form a sound absorbing layer, at least one ground connection part joined between the sound absorbing bodies, at least one center connection part joined between the sound absorbing bodies and including an electrode, a plurality of side connection parts joined between the sound absorbing bodies and disposed further outward than the center connection parts, the plurality of side connection parts each including an electrode, and a plurality of piezoelectric bodies disposed in front of the sound absorbing layer to be electrically connected to the ground connection part, the center connection part, and the side connection part.

A plurality of electrode layers may be formed on a surface of the sound absorbing layer.

The plurality of electrode layers may include at least one first electrode layer electrically connected to the ground connection part, a plurality of second electrode layers electrically connected to the side connection part, and at least one third electrode layer electrically connected to the center connection part.

The first electrode layer, the second electrode layer, and the third electrode layer may be formed to be separated from one another, and the second electrode layer and the third electrode layer may be electrically connected to the piezoelectric body below the piezoelectric body.

The center connection part may include a first center connection part, and a second center connection part including an electrode formed not to face an electrode of the first center connection part, the second center connection part being disposed apart from the first center connection part.

The side connection part may include a first side connection part and a second side connection part, and an electrode of the first side connection part and an electrode of the second side connection part may be formed to face each other.

The first side connection part may be disposed between the first center connection part and the ground connection part adjacent to the first center connection part, and the second side connection part may be disposed between the second center connection part and the ground connection part adjacent to the second center connection part.

Piezoelectric bodies electrically connected to the first center connection part and the second center connection part and piezoelectric bodies electrically connected to the side connection part may be spaced apart from each other.

A mounting groove may be formed in the sound absorbing layer, and the piezoelectric body may be inserted into the mounting groove.

The second electrode layer and the third electrode layer may be formed on a bottom side of the mounting groove.

The mounting groove may include a first separation groove formed in both sides of the mounting groove to separate the first electrode layer and the second electrode layer from each other, and a second separation groove formed in the bottom side of the mounting groove to separate the second electrode layer and the third electrode layer from each other.

A bottom side of the first separation groove and a bottom side of the second separation groove may be located below the second electrode layer and the third electrode layer.

An ultrasonic probe according to another aspect of the present disclosure includes a sound absorbing layer formed by arranging a plurality of sound absorbing bodies, and piezoelectric bodies bonded on the sound absorbing layer in a direction perpendicular to a direction in which the sound absorbing bodies are arranged, wherein the piezoelectric bodies include a plurality of center piezoelectric bodies and a plurality of side piezoelectric bodies spaced apart from the center piezoelectric bodies and disposed at a side of the piezoelectric bodies, and the sound absorbing layer includes a first center connection part configured to transmit a signal to some of the plurality of center piezoelectric bodies, a second center connection part configured to transmit a signal to the other piezoelectric bodies to which a signal is not transmitted from the first center connection part, and a plurality of side connection parts located further outward than the first center connection part and the second center connection part and configured to transmit a signal to the plurality of side piezoelectric bodies.

A high-resolution image may be obtained at a different position when a signal is transmitted to the plurality of center piezoelectric bodies and the plurality of side piezoelectric bodies from a position when a signal is transmitted only to the plurality of center piezoelectric bodies.

The ultrasonic probe may further include a switch for controlling a signal to be transmitted to the plurality of side piezoelectric bodies through the plurality of side connection parts, and a signal may not be transmitted to the plurality of side piezoelectric bodies when the switch is open and may be transmitted to the plurality of side piezoelectric bodies when the switch is closed.

A method of manufacturing an ultrasonic probe includes providing a plurality of sound absorbing bodies to form a sound absorbing layer, forming a plurality of electrodes spaced apart from first center connection parts joined between the plurality of sound absorbing bodies, forming a plurality of electrodes spaced apart from second center connection parts joined between the plurality of sound absorbing bodies to be spaced apart from the first center connection parts, forming electrodes on a plurality of side connection parts located further outward than the first center connection parts and the second center connection parts, providing a plurality of ground connection parts to be disposed further outward than the side connection parts, and forming the sound absorbing layer by joining the first center connection parts, the second center connection parts, the plurality of side connection parts, and the plurality of ground connection parts between the sound absorbing bodies.

The method may further include forming a mounting groove in a side of the sound absorbing layer, and forming an electrode layer in a side of the sound absorbing layer, in which the mounting groove is formed, to be electrically connected to the ground connection parts, the first center connection parts, the second center connection parts, and the side connection parts.

The method may further include forming a plurality of first separation grooves between the ground connection parts and the side connection parts to form a first electrode layer to be electrically connected to the ground connection parts through separation of the electrode layer.

The method may further include inserting a piezoelectric body into the mounting groove to be electrically connected to the electrode layer, the piezoelectric body being coupled to the electrode layer, and forming a plurality of second separation grooves between the first center connection part and the side connection part or between the second center connection part and the side connection part to form a plurality of piezoelectric bodies spaced apart from each other and electrically connected to a second electrode layer or a third electrode layer while forming the second electrode layer and the third electrode layer to be spaced apart from each other.

The method may further include forming a plurality of second separation grooves in the electrode layer to form a second electrode layer and a third electrode layer spaced apart from each other, forming a third separation groove in the piezoelectric body to correspond to the second separation grooves in the electrode layer, and inserting the piezoelectric body into the mounting groove such that the second separation grooves and the third separation grooves face each other.

Advantageous Effects

By connecting a plurality of electrodes to a piezoelectric body using an electrode layer instead of soldering work, connection work can be facilitated and performance degradation due to poor connection can be prevented.

Because a sound absorbing layer with an electrode can be formed independently, an ultrasonic probe can be manufactured by easily assembling other components, thereby reducing manufacturing costs and facilitating the manufacture of the ultrasonic probe.

DESCRIPTION OF DRAWINGS

FIG. 1 is a perspective view of an ultrasonic imaging device according to an embodiment.

FIG. 2 is a diagram schematically illustrating a configuration of the ultrasonic probe of FIG. 1.

FIG. 3 is a cross-sectional view taken along line X-X' of FIG. 2.

FIG. 4 is an exploded perspective view of a sound absorbing layer of FIG. 2.

FIG. 5 is a cross-sectional view of electrodes on a plane in a lateral direction L and an elevation direction E.

FIG. 6 is a cross-sectional view of an ultrasonic probe according to another embodiment.

FIG. 7 is a diagram illustrating a part of a circuit of the ultrasonic probe of FIG. 2.

FIG. 8 is a diagram illustrating a part of a circuit of the ultrasonic probe of FIG. 6 according to an embodiment.

FIG. 9 is a diagram illustrating a part of a circuit of the ultrasonic probe of FIG. 6 according to another embodiment.

FIG. 10 is a flowchart of a method of manufacturing the ultrasonic probe of FIG. 2.

FIG. 11 is a diagram of a state in which a mounting groove is formed in the method of FIG. 10.

FIG. 12 is a diagram of a state in which an electrode layer is formed in the method of FIG. 10.

FIG. 13 is a diagram of a state in which a first separation groove is formed in the method of FIG. 10.

FIG. 14 is a diagram of a state in which a piezoelectric body is provided in the method of FIG. 10.

FIG. 15 is a diagram of a state in which a second separation groove is formed in the method of FIG. 10.

FIG. 16 is a flowchart of another example of a method of manufacturing the ultrasonic probe of FIG. 2.

FIG. 17 is a diagram of a state in which a third separation groove is formed in the method of FIG. 10.

MODES OF THE INVENTION

Embodiments described herein and configurations shown in the appended drawings are only examples of the present disclosure, and there may be a variety of modified examples that replace the embodiments and drawings of the present disclosure at the time of filing the present disclosure.

The same reference numerals or signs in each of the drawings of the present disclosure denote components or elements that perform substantially the same functions. In the drawings, the shape and size of each element may be exaggerated for clarity.

The terms used herein are only used to describe embodiments and are not intended to limit the present disclosure. As used herein, singular expressions are intended to include plural forms as well, unless the context clearly dictates otherwise. It should be understood that the terms "comprise" and/or "comprising," when used herein, specify the presence of stated features, integers, steps, operations, elements, components, or combinations thereof, but do not preclude the presence or addition of one or more features, integers, steps, operations, elements, components, or combinations thereof.

Terms including ordinal numbers such as "first" and "second" may be used herein to describe various components, but the components are not limited by the terms and the terms are used only to distinguish one component from another. For example, a first component may be referred to as a second component without departing from the scope of the present disclosure, and similarly, a second component may also be referred to as a first component. The term "and/or" includes a combination of a plurality of related items described herein or any one of the plurality of related items.

Terms such as "forward," "rearward," "upper," and "lower" are defined based on the drawings, and the shape and position of each component are not limited by the terms.

Reference numerals assigned to operations are used only for convenience of description rather than describing an order of the operations and thus these operations may be performed in an order different from that described above unless the context indicates a specific order.

Hereinafter, embodiments of the present disclosure will be described in detail with reference to the accompanying drawings.

FIG. 1 is a perspective view of an ultrasonic imaging device according to an embodiment.

Referring to FIG. 1, the ultrasonic imaging device 10 includes an ultrasonic probe 100 that transmits an ultrasonic signal to a subject, receives an ultrasonic echo signal from the subject, and converts the ultrasonic echo image into an electrical signal, and a main body 200 that generates an ultrasonic image on the basis of the ultrasonic signal. The main body 200 may be connected to the ultrasonic probe 100 through a wired communication network or a wireless communication network. The main body 200 may be a workstation that includes a display 300 and an input device 400.

The ultrasonic probe 100 includes a transducer module 110 that is included in a housing h, emits sound waves to a subject, receives ultrasonic echo waves reflected from the subject, and converts an electrical signal into sound waves and vice versa, a male connector 130 that is physically coupled to a female connector of the main body 200 to transmit a signal to or receive a signal from the main body 200, and a cable 120 that connects the male connector 130 and the transducer module 110.

Here, the subject may be biological tissue such as the body, blood vessel, bone, or muscle of a human or an animal, but is not limited thereto and may be anything of which an image of an internal structure can be obtained by the ultrasonic imaging device 10.

In addition, the ultrasonic probe 100 may be connected to the main body 200 through a wireless communication network to receive various types of signals necessary to control the ultrasonic probe 100 or transmit an analog signal or a digital signal corresponding to an ultrasonic echo signal received by the ultrasonic probe 100. The wireless communication network is a communication network through which signals are received and transmitted wirelessly.

Ultrasonic echo waves are ultrasonic waves reflected from a subject to which ultrasonic waves are emitted, and have a variety of frequency bands and various energy levels for producing various ultrasonic images according to diagnostic modes.

The transducer module 110 may generate ultrasonic waves according to alternating-current (AC) power supplied thereto. Specifically, the transducer module 110 may be supplied with AC power from an external power supply or an internal power storage device, e.g., a battery. An oscillator of the transducer module 110 may oscillate to generate ultrasonic waves according to the supplied AC power.

Three directions that form right angles with respect to the center of the transducer module 110 may be defined as an axial direction A, a lateral direction L, and an elevation direction E. Specifically, a direction in which ultrasonic waves are emitted may be defined as the axial direction A, a direction in which the transducer modules 110 are formed in rows may be defined as the lateral direction L, and a direction perpendicular to the axial direction A and the lateral direction L may be defined as the elevation direction E. The transducer modules 110 may be formed in rows in the elevation direction E, thereby forming a multi-row array.

The transducer module 110 and the male connector 130 are connected through the cable 120 by connecting the transducer module 110 to one end of the cable 120 and the male connector 130 to the other end of the cable 120.

The male connector 130 may be physically connected to the female connector 201 of the main body 200 by connecting the male connector 130 to the other end of the cable 120. The male connector 130 transmits an electrical signal generated by the transducer module 110 to the female connector 201 physically coupled thereto or receives a control signal generated by the main body 200 from the female connector 201.

However, when the ultrasonic probe 100 is embodied as a wireless ultrasonic probe 100, the cable 120 and the male connector 130 may be omitted and signals may be transmitted or received between the ultrasonic probe 100 and the main body 200 through an additional wireless communication module (not shown), and therefore, embodiments are not limited to the ultrasonic probe 100 shown in FIG. 1.

The main body 200 may establish wireless communication with the ultrasonic probe 100 through at least one of a short-range communication module and a mobile communication module.

The short range communication module is a module for establishing short-range communication within a certain distance. For example, short-range communication technologies include, but are not limited to, wireless local area network (LAN), Wi-Fi, Bluetooth, ZigBee, Wi-Fi Direct (WFD), Ultra-Wideband (UWB), Infrared Data Association (IrDA), Bluetooth Low Energy (BLE)), near-field communication (NFC), etc.

The mobile communication module may transmit a radio signal to or receive a radio signal from at least one of a base station, an external terminal, and a server via a mobile communication network. Here, the radio signal is a signal containing various types of data. That is, the main body 200 may exchange signals containing various types of data with the ultrasonic probe 100 through at least one of a base station and a server.

For example, the main body 200 may exchange signals containing various types of data with the ultrasonic probe 100 through a server in a mobile communication network such as a 3G or 4G network. Alternatively, the main body 200 may exchange data from a hospital server or a medical device in a hospital connected thereto through a medical picture archiving and communication system (PACS). Alternatively, the main body 200 may exchange data according to a Digital Imaging and Communications in Medicine (DICOM) standard but is not limited thereto.

Alternatively, the main body 200 may exchange data with the ultrasonic probe 100 through a wired communication network. The wired communication network is a communication network through which signals are received and transmitted via wire. According to an embodiment, the main body 200 may exchange various types of signals with the ultrasonic probe 100 using a wired communication network such as Peripheral Component Interconnect (PCI), PCI-Express or Universal Serial Bus (USB) but is not limited thereto.

In the main body 200 of the ultrasonic imaging device 10, a display 300 and an input unit 400 may be included. Various control commands may be received from a user through the input unit 400, as well as setting information about the ultrasonic probe 100.

The setting information about the ultrasonic probe 100 includes gain information, zoom information, focus information, time gain compensation (TGC) information, depth information, frequency information, power information, frame average information, dynamic range information, etc. However, the setting information about the ultrasonic probe 100 is not limited thereto and includes various types of information that may be set to capture an ultrasonic image.

The information described above may be transmitted to the ultrasonic probe 100 through a wireless or wired communication network, and the ultrasonic probe 100 may be set according to the transmitted information. In addition, the main body 200 may receive various control commands, such as a command to transmit an ultrasonic signal, from a user through the input unit 400 and transmit the various control commands to the ultrasonic probe 100.

The input unit 400 may be embodied as a keyboard, a foot switch or a foot pedal. For example, the keyboard may be implemented as hardware. The keyboard may include at least one of a switch, a key, a joystick and a trackball. As another example, the keyboard may be embodied as software such as a graphical user interface. In this case, the keyboard may be displayed through the display 300. The foot switch or the foot pedal may be provided below the main body 200, and a user may control an operation of the ultrasonic imaging device 10 using the foot pedal.

The display 300 may be embodied in any of various well-known forms such as a cathode ray tube (CRT), a liquid crystal display (LCD), a light-emitting diode (LED), a plasma display panel (PDP), and an organic LED (OLED), but is not limited thereto.

The display 300 may display an ultrasonic image of a target region in a subject. The ultrasonic image displayed on the display 300 may be a two-dimensional (2D) or three-dimensional (3D) ultrasonic image, and various ultrasonic images may be displayed according to an operating mode of the ultrasonic imaging device 10. The display 300 may display not only a menu or guide necessary to make an ultrasonic diagnosis but also information about an operational state of the ultrasonic probe 100.

Ultrasonic images include not only an amplitude mode (A-mode) image, a brightness mode (B-mode) image, and a motion mode (M-mode) image but also a color mode (C-mode) image, and a Doppler-mode (D-mode) image.

The A-mode image is an ultrasonic image showing a size of an ultrasonic signal corresponding to an ultrasonic echo signal, the B-mode image is an ultrasonic signal showing the size of the ultrasonic signal corresponding to the ultrasonic echo signal using a brightness level, and the M-mode image is an ultrasonic signal showing movement of a subject at a certain position over time. The D-mode image is an ultrasonic image showing a moving subject in the form of waveform form using the Doppler effect, and the C-mode image is an ultrasonic image showing the moving subject in the form of color spectrum.

When the display 300 is embodied as a touch screen type, the display 300 may also perform a function of the input unit 400. That is, the main body 200 may receive various commands from a user through at least one of the display 300 and the input unit 400.

In addition, although not shown, the main body 200 may be provided with a voice recognition sensor to receive a voice command from a user. A configuration of the ultrasonic probe 100 will be described in detail below, focusing on a configuration of the transducer module 110.

FIG. 2 is a diagram schematically illustrating a configuration of the ultrasonic probe of FIG. 1. FIG. 3 is a cross-sectional view taken along line X-X' of FIG. 2. FIG. 4 is an exploded perspective view of a sound absorbing layer of FIG. 2. FIG. 5 is a cross-sectional view of electrodes on a plane in a lateral direction L and an elevation direction E.

The ultrasonic probe 100 shown in FIGS. 2 to 5 may include a sound absorbing layer 500 and a piezoelectric body 600. The sound absorbing layer 500 may be disposed behind the piezoelectric body 600. The sound absorbing layer 500 may suppress free vibration of the piezoelectric body 600 to reduce a pulse width of ultrasonic waves, and block undesired propagation of the ultrasonic waves to the rear of the piezoelectric body 600 to prevent distortion of an image.

The sound absorbing layer 500 may include sound absorbing bodies 510. The sound absorbing bodies 510 may include a plurality of sound absorbing bodies 511, 512, 513, 514, 515, 516, and 517 and be formed by joining the sound absorbing bodies 510. Specifically, the sound absorbing bodies 510 may be arranged and stacked in the altitude direction E. The sound absorbing layer 500 may be formed of a material containing rubber to which epoxy resin and tungsten powder are added.

The piezoelectric body 600 may be provided on a front side of the sound absorbing layer 500. That is, the piezoelectric body 600 may be provided on one side of the sound absorbing layer 500 in a direction perpendicular to a direction in which the sound absorbing bodies 510 are arranged. The piezoelectric body 600 may include a plurality of piezoelectric bodies 600.

A mounting groove 520 may be formed on a front side of the sound absorbing layer 500, and the piezoelectric body 600 may be inserted into the mounting groove 520. The mounting groove 520 may be formed on the front side of the sound absorbing layer 500 to have a concave shape corresponding to the piezoelectric body 600, so that the piezoelectric body 600 may be inserted into the mounting groove 520.

The plurality of piezoelectric bodies 600 may be arranged in an array to be used as a multi-channel. Specifically, piezoelectric bodies 600 separated by a plurality of separation grooves 530 extending in the lateral direction L may be arranged in the elevation direction E, and piezoelectric bodies separated by a plurality of kerfs 540 extending in the elevation direction E by dicing may be arranged in the lateral direction L. Although not shown in FIG. 2, the kerfs 540 may be formed in an area B.

The kerfs 540 may be formed at a position at which a separation line D of FIG. 5 is shown. Therefore, in FIG. 5, the separation line D and the kerf 540 may be considered as the same component. A plurality of piezoelectric bodies 600 in a region between two adjacent kerfs d (hereinafter referred to as "column C") may be arranged in the elevation direction E, a plurality of piezoelectric bodies 600 may be arranged in each of a plurality of columns C in the elevation direction E, and the same array of piezoelectric bodies 600 may be arranged in each of the plurality of columns C in the elevation direction E. The piezoelectric bodies 600, an electrode layer 700, a sound matching layer 800, etc. to be described below may be separated by the kerf 540.

The ultrasonic probe 100 may include at least one center connection part 550, a plurality of side connection parts 560, and at least one ground connection part 570. The at least one center connection part 550 and the side connection parts 560 may be joined and arranged between the plurality of sound absorbing bodies 510, 511, 512, 513, 514, 515, 516, and 517. The at least one ground connection part 570 may be joined and arranged between the plurality of sound absorbing bodies 510, 511, 512, 513, 514, 515, 516, and 517. That is, the sound absorbing layer 500 may include a center connection part 550, a side connection part 560, and a ground connection part 570.

Specifically, the center connection part 550 may be provided inside the sound absorbing layer 500, the side connection part 560 may be provided outside the center connection part 550, and the ground connection part 570 may be provided outside the side connection part 560. In other words, the ground connection part 570 may be provided on an outermost side of the sound absorbing layer 500, the center connection part 550 may be provided on an innermost side of the sound absorbing layer 500, and the side connection part 560 may be provided between the ground connection part 570 and the center connection part 550.

The ground connection part 570 includes an insulating part (not shown) and an electrode 570a. The ground connection part 570 is bonded between the sound absorbing bodies 510, 511, 512, 513, 514, 515, 516, and 517. According to the drawings, the ground connection part 570 may include a plurality of ground connection parts 570 and may be joined between the sound absorbing bodies 511 and 512 or between other sound absorbing bodies 516 and 517. However, embodiments are not limited thereto and the ground connection parts 570 may be formed outside the sound absorbing layer 500. That is, the ground connection parts 570 may be arranged outside the sound absorbing bodies 511 and 517.

The electrode 570a may be formed on one side of the ground connection part 570. A plurality of electrodes 570a of the ground connection parts 570 may be formed in the lateral direction L to correspond to an array of piezoelectric bodies 600 in the lateral direction L. However, embodiments are not limited thereto and one side of the ground connection part 570 may correspond to the electrode 570a.

The center connection part 550 may include a first center connection part 551 and a second center connection part 552.

First center connection parts 551 may be joined between the sound absorbing bodies 513 and 514. According to the drawings, the first center connection parts 551 may be inserted and joined between the two sound absorbing bodies 513 and 514 among seven sound absorbing bodies 511, 512, 513, 514, 515, 516, and 517.

The first center connection part 551 includes an insulating part (not shown) and an electrode 551a. The electrode 551a may be formed on one side of the first center connection part 551. A plurality of electrodes 551a may be provided on the insulating part to be spaced apart from each other in the lateral direction L. The electrode 551a of the first center connection part 551 may be a signal electrode electrically connected to a first electrode 601 of the piezoelectric body 600 described below.

The first center connection part 551 may include a flexible printed circuit board (PCB) and may further include a PCB and other components for supplying a signal or electric power.

One end of each of the first center connection parts 551 joined between the sound absorbing bodies 513 and 514 is exposed in front of the sound absorbing layer 500 adjacent to the piezoelectric body 600, and another end thereof extends to the outside of the sound absorbing layer 500 through the rear of the sound absorbing layer 500. Because one end of the first center connection part 551 is exposed in front of the sound absorbing layer 500, the electrode 551a of the first center connection part 551 may be exposed to the outside in front of the sound absorbing layer 500.

Second center connection parts 552 may be joined between the sound absorbing bodies 514 and 515. According to the drawings, the second center connection parts 551 may be inserted and joined between the two sound absorbing bodies 514 and 515 among seven sound absorbing bodies 511, 512, 513, 514, 515, 516, and 517.

The second center connection parts 552 may be disposed apart from the first center connection parts 551. Specifically, because the sound absorbing body 514 is disposed between the second center connection part 552 and the first center connection part 551, the second center connection part 552 may be spaced apart from the first center connection part 551 by a space occupied by the sound absorbing body 514 in the elevation direction E.

The second center connection part 552 includes an insulating part (not shown) and an electrode 552a. The electrode 552a may be formed on one side of the second center connection part 552. A plurality of electrodes 552a of the second center connection parts 552 are provided on the insulating part apart from each other in the lateral direction L. Specifically, the electrode 552a of the second center connection part 552 may be formed not to face the electrode 551a of the first center connection part 551. The electrode 552a of the second center connection part 552 may be a signal electrode electrically connected to the first electrode 601 of the piezoelectric body 600 described below.

The second center connection part 552 may include a flexible PCB and may further include a PCB and other components for supplying a signal or electric power.

One end of each of the second center connection parts 552 joined between the sound absorbing bodies 514 and 515 is exposed in front of the sound absorbing layer 500 adjacent to the piezoelectric body 600, and another end thereof extends to the outside of the sound absorbing layer 500 through the rear of the sound absorbing layer 500. Because one end of the second enter connection part 552 is exposed in front of the sound absorbing layer 500, the electrode 552a of the second center connection part 552 may be exposed to the outside in front of the sound absorbing layer 500.

The side connection part 560 may be formed inside the sound absorbing layer 500. Specifically, the side connection part 560 may include a first side connection part 561 and a second side connection part 562. However, embodiments are not limited thereto and four or six side connection parts 560 may be provided.

The side connection parts 561 and 562 may include an insulating part (not shown) and electrodes 561a and 562a. The electrodes 561a and 562a may be formed on one side of the side connection part 560. A plurality of electrodes 561a and 562a of the side connection parts 561 and 562 may be formed in the lateral direction L to correspond to an array of piezoelectric bodies 600 in the lateral direction L.

Specifically, the electrodes 561a of the first side connection part 561 and the electrodes 562a of the second side connection part 562 may be provided to face each other. That is, one electrode 561a of the first side connection part 561 and one electrode 562a of the second side connection part 562 may be provided in each of the columns C. However, embodiments are not limited thereto, and one side of the side connection part 561 and one side of the side connection part 562 may correspond to the electrodes 561a and 562a, respectively.

The side connection part 560 may include a flexible PCB and may further include a PCB and other components for supplying a signal or electric power.

The columns C separated by the kerfs 540 may have sufficient strength and narrower pitches, thus achieving high density and small columns C, because the center connection parts 551 and 552, the side connection parts 561 and 562, and the ground connection part 570 are bonded on the sound absorbing layer 500, and the electrode 551a and the electrode 552a of the second center connection part 552 are misaligned with each other as described above.

Because the PCBs of the connection parts 550, 560 and 570 are not disposed horizontally between the sound absorbing layer 500 and the piezoelectric body 600 but may be disposed vertically inside the sound absorbing layer 500, degradation of performance, e.g., a spatial resolution, when the PCBs are disposed horizontally between the sound absorbing layer 500 and the piezoelectric body 600 may be prevented.

The sound absorbing layer 500 may include the electrode layer 700 on a front side thereof. The electrode layer 700 may include a first electrode layer 701, a second electrode layer 702, and a third electrode layer 703. The first electrode layer 701, the second electrode layer 702, and the third electrode layer 703 may be separated from one another due to the separation groove 530. The second electrode layer 702 and the third electrode layer 703 may be formed on a bottom surface of the mounting groove 520, and the first electrode layer 701 may be formed on both sides of the mounting groove 520.

The first electrode layer 701, the second electrode layer 702, and the third electrode layer 703 may be formed of a highly conductive metal such as gold, silver or copper and may be formed by deposition, sputtering, plating or spraying. The first electrode layer 701, the second electrode layer 702, and the third electrode layer 703 may be formed by forming one electrode layer 700 and dividing the electrode layer 700 or may be formed separately from one another.

However, embodiments are not limited thereto. FIG. 6 is a cross-sectional view of an ultrasonic probe according to another embodiment. Description of parts that are the same as those described above is omitted here.

Referring to FIG. 6, a side connection part 560 of the ultrasonic probe may further include a third side connection part 563 and a fourth side connection part 564.

In this case, a fourth electrode layer 704 electrically connected to the third side connection part 563 and the fourth side connection part 564 may be further provided. In addition, a side piezoelectric body 600c electrically connected to the third side connection part 563 or the fourth side connection part 654 through the fourth electrode layer 704 may be further provided.

As shown in FIG. 6, the third side connection part 563 and the fourth side connection part 564 may be disposed between the sound absorbing bodies 512, 518, 519, and 516 and joined.

A separation groove 533 may be formed to separate the side piezoelectric body 600c connected to the third or fourth side connection part 563 or 564 from the side piezoelectric body 600b connected to the first or second side connection part 561 or 562.

The ultrasonic probe may further include a sound matching layer 800. The sound matching layer 800 is disposed in front of the piezoelectric body 600. The sound matching layer 800 matches sound impedance of the piezoelectric body 600 and sound impedance of a subject to effectively transmit an ultrasonic signal generated by the piezoelectric body 600 to the subject, and may be provided to achieve an intermediate value of the sound impedance of the piezoelectric body 600 and the sound impedance of the subject.

The sound matching layer 800 may be formed of glass or a resin material and may include a first sound matching layer 801 and a second sound matching layer 802 formed of different materials so that sound impedance may gradually change from the piezoelectric body 600 to the subject.

The sound matching layer 800 may include an electrode part 810. The electrode part 810 may be disposed between the first sound matching layer 801 and the piezoelectric body 600 to be connected to the piezoelectric body 600. The electrode part 810 may be formed of a highly conductive metal such as gold, silver or copper, and may be formed by deposition, sputtering, plating or spraying.

Although not shown, the ultrasonic probe may further include a lens layer disposed in front of the sound matching layer 800 to focus an ultrasonic signal traveling forward on a certain point.

The first center connection part 551, the second center connection part 552, the side connection part 560, and the ground connection part 570 may be electrically connected to the piezoelectric body 600. This will be described in detail below.

The piezoelectric body 600 may include the first electrode 601 on a lower side of the piezoelectric body 600 and a second electrode 602 on an upper side thereof. The piezoelectric body 600 may be electrically connected to the first center connection part 551, the second center connection part 552, or the side connection part 560.

The third electrode layer 703 may be electrically connected to the electrode 551a of the first center connection part 551 or the electrode 552a of the second center connection part 552, which is exposed in front of the sound absorbing layer 500. The piezoelectric body 600 may include a center piezoelectric body 600a, and a first electrode 601 of the center piezoelectric body 600a may be electrically connected to the electrode 551a of the first center connection part 551 or the electrode 552a of the second center connection part 552 through the third electrode layer 703.

More specifically, the piezoelectric body 600 is divided into a plurality of columns C by the kerfs 540 formed by dicing. The third electrode layer 703 and the center piezoelectric body 600a are provided in each of the plurality of columns C. Because the electrode 551*a* of the first center connection part 551 and the electrode 552*a* of the second center connection part 552 are arranged to be misaligned by one column C in the lateral direction L, the first electrode 601 of the center piezoelectric body 600*a* and the third electrode layer 703 in each of the plurality of columns C may be electrically connected to the electrode 551*a* of the first center connection part 551 or the electrode 552*a* of the second center connection part 552.

The second electrode layer 702 may be electrically connected to the electrode 560*a* of the side connection part 560 exposed in front of the sound absorbing layer 500. The piezoelectric body 600 may include a side piezoelectric body 600*b*, and a first electrode 601 of the side piezoelectric body 600*b* may be electrically connected to the electrode 560*a* of the side connection part 560 through the second electrode layer 702.

Because the electrode 560*a* of the side connection part 560 is formed to correspond to all of the columns C, the electrode 560*a* of the side connection part 560 may be disposed in each of the plurality of columns C.

The first electrode layer 701 may be electrically connected to the electrode 570*a* of the ground connection part 570 exposed in front of the sound absorbing layer 500. Because the electrode 570*a* of the ground connection part 570 is formed to correspond to all of the columns C, the electrode 570*a* of the ground connection part 560 may be disposed in each of the plurality of columns C.

The electrode part 810 of the sound matching layer 800 may be electrically connected to the second electrode 602 of the piezoelectric body 600 and the first electrode layer 701. The piezoelectric body 600 may be electrically connected to the electrode part 810 due to the electrical connection described above. Specifically, the electrode part 810 of the sound matching layer 800 in each of the plurality of columns C may be electrically connected to the second electrode 602 and the first electrode layer 701 in a corresponding column C, and may be separated from the second electrode 602 and the first electrode layer 701 in another column C not to be electrically connected thereto.

Although the electrode part 810 of the ultrasonic probe 100 is illustrated in the drawings as being formed in the rear of the first sound matching layer 810 adjacent to the piezoelectric body 600, embodiments are not limited thereto and may be embodied in many different forms. For example, the sound matching layer 800 may be provided to include the electrode part 810 surrounding the entire sound matching layer 800 or a part of or the entire sound matching layer 800 (e.g., the first sound matching layer 801) may be formed of a conductive material so that the sound matching layer 800 may be electrically connected to the piezoelectric body 600.

FIG. 7 is a diagram illustrating a part of a circuit of the ultrasonic probe of FIG. 2. FIG. 8 is a diagram illustrating a part of a circuit of the ultrasonic probe of FIG. 6 according to an embodiment. FIG. 9 is a diagram illustrating a part of a circuit of the ultrasonic probe of FIG. 6 according to another embodiment.

Referring to FIGS. 7 to 9, a configuration of an ultrasonic probe will be described below in terms of controlling the ultrasonic probe.

Referring to FIG. 7, the ultrasonic probe may include a plurality of connectors 900 to be electrically connected to a center piezoelectric body 600*a* or a side piezoelectric body 600*b* through a center connection part 550 or a side connection part 560.

The ultrasonic probe 100 may include a pulser (not shown) for generating a voltage of a certain frequency, and the connector 900 may transmit a voltage generated by the pulses to the piezoelectric body 600. The piezoelectric body 600 may vibrate according to an amplitude and frequency of the voltage output from the pulses to produce an ultrasonic wave.

The connector 900 may include a first connector 901 connected to the center connection part 550, a second connector 902 connected to the first side connection part 561, and a third connector 903 connected to the second side connection part 562. The connector 900 shown in the drawings is provided in one column C. Accordingly, the first connector 901 may be connected to the first center connection part 551 or the second center connection part 552 according to an electrode of the center connection part 550 in the column C. FIG. 7 illustrates an example in which the first connector 901 is connected to the electrode 551*a* of the first center connection part 551.

Each connector 900 may be electrically connected to the electrodes of the connection parts 550 and 560 connected thereto. That is, the first connector 901 may be electrically connected to the electrode 551*a* of the first center connection part 551 or the electrode 552*a* of the second center connection part 552, the second connector 902 may be electrically connected to the electrode 561*a* of the side connection part 561, and the third connector 903 may be electrically connected to the electrode 562*a* of the second side connection part 562*a*.

As such, the connector 900 may be a separate wire or electrode but is not limited thereto, and the electrodes 551*a*, 552*a*, 561*a*, and 562*a* of the connection parts 551, 552, 561, and 562 may correspond to the connector 900. That is, the structure of the connector shown in FIGS. 7 to 9 may be a schematic view of a shape of a circuit implemented in a general manner.

The second connector 902 and the third connector 903 may be electrically connected in parallel and may be electrically connected to the first connector 901 while connected in parallel to each other. A switch 910 may be provided between the first connector 901 and the second and third connectors 902 and 903 that are electrically connected in parallel. The switch 910 may be opened or closed to transmit a signal generated by the pulser to the second and third connectors 902 and 903 or to block the transmission of the signal by a physical or electronic method, thereby controlling the supply of a signal to the side piezoelectric body 600*b* using the side connection parts 561 and 562.

When the switch 910 is open, only the first connector 901 may transmit and receive signals. That is, only the center piezoelectric body 600*a* may generate ultrasonic waves. In this case, a high-resolution image of a near-field in a direction of depth of a subject may be obtained using an ultrasonic signal generated by the piezoelectric body 600*a*.

When the switch 910 is closed, all of the first to third connectors 901, 902, and 903 may transmit and receive signals. That is, ultrasonic waves may be generated through vibration of the side piezoelectric body 600*b* and the center piezoelectric body 600*a*. In this case, a high-resolution image of a far-field in the direction of depth of the subject may be obtained using ultrasonic signals generated by the piezoelectric bodies 600.

A processor (not shown) that may be provided inside the main body 200 or at another position may obtain a high-resolution image of all regions of the subject by collecting, synthesizing or editing a near-field image obtained when the switch 910 is open and a far-field image obtained when the switch 910 is closed.

However, embodiments are not limited thereto, and a part of a subject of which a high-resolution image is obtainable may vary according to whether the switch 910 is open or closed, and a high-resolution image of all regions of the subject may be obtained using high-resolution images obtained when the switch 910 is open and when the switch 910 is closed.

Referring to FIG. 8, the ultrasonic probe may further include a third side connection part 563 and a fourth side connection part 564. The ultrasonic probe may further include a fourth connector 904 electrically connected to an electrode 563*a* of the third side connection part 563 and a fifth connector 905 electrically connected to an electrode 564*a* of the fourth side connection part 564. The second connector 902 and the third connector 903 may be electrically connected in parallel, and the fourth connector 904 and the fifth connector 905 may be electrically connected to each other.

The second connector 902 and the third connector 903 may be electrically connected to the first connector 901 while connected in parallel to each other. A first switch 910 may be provided between the first connector 901 and the second and third connectors 902 and 903 that are electrically connected in parallel. The fourth connector 904 and the fifth connector 905 may be electrically connected to the first connector 901 while connected in parallel to each other. A second switch 920 may be provided between the first connector 901 and the fourth and fifth connectors 904 and 905 that are electrically connected in parallel.

When the first switch 910 is open and the second switch 920 is closed, only the first connector 901, the fourth connector 904, and the fifth connector 905 may transmit and receive signals. That is, ultrasonic waves may be generated through vibration of the side piezoelectric body 600*c* and the center piezoelectric body 600*a*. In this case, a high-resolution image of a near-field in a direction of depth of a subject may be obtained using ultrasonic signals generated by the piezoelectric bodies 600.

When the second switch 920 is open and the first switch 910 is closed, only the first connector 901, the second connector 902, and the third connector 903 may transmit and receive signals. That is, ultrasonic waves may be generated through vibration of the side piezoelectric body 600*b* and the center piezoelectric body 600*a*. In this case, a high-resolution image of a far-field in the direction of depth of the subject may be obtained using ultrasonic signals generated by the piezoelectric bodies 600.

However, embodiments are not limited thereto. For example, a high-resolution image of a far-field may be obtained when the first switch 910 is open and the second switch 920 is closed, and a high-resolution image of a near-field may be obtained when the second switch 920 is open and the first switch 910 is closed.

A processor (not shown) may compare images obtained in various cases, and obtain a high-resolution image of all regions of a subject by collecting, synthesizing or editing a highest-resolution image of the near-field and a highest-resolution image of the far-field. That is, a high-resolution image of all of the regions of the subject in a depth direction may be obtained by comparing images in various cases and using a highest-resolution image at a certain depth.

Another example will be provided. There may be a case in which both the first switch 910 and the second switch 920 are opened to vibrate only the center piezoelectric body 600*a*, a case in which only the first switch 910 is closed to vibrate only the center piezoelectric body 600*a* and the side piezoelectric body 600*b*, and a case in which the first and second switches 910 and 920 are closed to vibrate all of the piezoelectric bodies 600*a*, 600*b* and 600*c*.

In these cases, high-resolution images of different regions in a direction of depth of a subject may be obtained. That is, a high-resolution image of all of the regions of the subject in the depth direction may be obtained by comparing images in these cases and using a highest-resolution image at a certain depth.

However, embodiments are not limited thereto. As shown in FIG. 9, the first connector 901, the second and third connectors 902 and 903 connected in parallel, and the fourth and fifth connectors 904 and 905 connected in parallel may be provided to transmit and receive signals independently. A signal or signals to be transmitted may be generated by one pulser or a plurality of pulsers.

The piezoelectric bodies 600*b* and 600*c* and the side connection parts 561, 562, 563, and 564 may be provided at left and right sides of the center piezoelectric body 600*a* and the center connection part 550 and controlled as described above to increase the performance of the ultrasonic probe and improve the quality of an ultrasonic image.

FIG. 10 is a flowchart of a method of manufacturing the ultrasonic probe of FIG. 2. FIG. 11 is a diagram of a state in which a mounting groove is formed in the method of FIG. 10. FIG. 12 is a diagram of a state in which an electrode layer is formed in the method of FIG. 10. FIG. 13 is a diagram of a state in which a first separation groove is formed in the method of FIG. 10. FIG. 14 is a diagram of a state in which a piezoelectric body is provided in the method of FIG. 10. FIG. 15 is a diagram of a state in which a second separation groove is formed in the method of FIG. 10.

A method of manufacturing the ultrasonic probe 100 will be described with reference to FIGS. 10 to 15 below.

According to the method of manufacturing the ultrasonic probe 100 according to the flowchart of FIG. 10, a sound absorbing layer 500 may be provided (S110).

The sound absorbing layer 500 may be provided by bonding a first center connection part 551 and a second center connection part 552 on both sides of a sound absorbing body 514 disposed at a center, bonding sound absorbing bodies 513 and 515 on sides of the first center connection part 551 and the second center connection part 552, bonding a side connection par 560 on sides of the sound absorbing bodies 513 and 515, bonding sound absorbing bodies 512 and 516 on sides of the side connection part 560, bonding a ground connection part 570 on sides of the sound absorbing bodies 512 and 516, and bonding sound absorbing bodies 511 and 517 on sides of the ground connection part 570.

The sound absorbing bodies 511, 512, 513, 514, 515, 516 and 517 may be formed of a material containing rubber to which epoxy resin, tungsten powder, etc. are added. However, embodiments are not limited thereto.

The provision of the sound absorbing layer 500 may include forming electrodes 551*a* and 552*a* on the first center connection part 551 and the second center connection part 552. As shown in FIG. 11, a plurality of electrodes 551*a* may be formed on the first center connection part 551 to be spaced apart from each other in the lateral direction L, and a plurality of electrodes 552*a* may be formed on the second center connection part 552 to be misaligned with the electrodes 551*a* of the first center connection part 551.

A front side of the sound absorbing layer 500 provided as described above may be flat. Thus, a mounting groove 520 may be formed by cutting the sound absorbing layer 500 such that the front side of the sound absorbing layer 500 may have a concave shape (S120). The mounting groove 520 may be formed in the sound absorbing layer 500 to have a shape corresponding to a piezoelectric body 600, so that the piezoelectric body 600 may be inserted into the mounting groove 520.

However, embodiments are not limited thereto. Referring to FIGS. 4 and 7, for example, the sound absorbing bodies 512 and 516 adjacent to the sound absorbing bodies 511 and 517 located at outermost sides may be provided to form steps, so that mounting grooves 520 may be formed by the sound absorbing bodies 510, 511, 512, 513, 514, 515, 516 and 517. The sound absorbing bodies 513, 514, and 515 disposed inward as compared to the sound absorbing bodies 512 and 516 forming steps may have a height corresponding to lower sides of the sound absorbing bodies 512 and 516, and the sound absorbing bodies 511 and 517 disposed outward as compared to the sound absorbing bodies 512 and 516 may have a height corresponding to upper sides of the sound absorbing bodies 512 and 516.

In addition, electrodes 551a and 552a may be formed on the first center connection part 551 and the second center connection part 552, and the side connection part 560 and the ground connection part 570 may be provided.

As shown in the drawings, the sound absorbing layer 500 may be provided by joining the first center connection part 551, the second center connection part 552, the side connection part 560, and the ground connection part 570 between the sound absorbing bodies 511, 512, 513, 514, 515, 516, and 517. A mounting groove 520 is formed in the sound absorbing layer 500 formed as described above.

As described above, the order in which the sound absorbing layer 500 is provided and the mounting groove 520 is formed is not limited, and they may be performed at the same time.

An electrode layer 700 may be formed on the sound absorbing layer 500 in which the mounting groove 520 is formed (S130).

The electrode 551a of the first center connection part 551, the electrode 552a of the second center connection part 552, and the electrode 560a of the side connection part 560 may be exposed on a bottom side of the mounting groove 520, and the electrode 570a of the ground connection part 570 may be exposed on stepped portions at both sides of the mounting groove 520. When the electrode layer 700 is formed on the front side of the sound absorbing layer 500, the electrode layer 700 may be electrically connected to the electrodes 551a, 552a, 560a, and 570a.

The electrode layer 700 may be formed of a highly conductive metal such as gold, silver or copper, and may be formed by deposition, sputtering, plating or spraying. However, embodiments are not limited thereto and various other methods may be used to stack the highly conductive metal on the front side of the sound absorbing layer 500.

The electrode layer 700 may be integrally formed with the front side of the sound absorbing layer 500, including the bottom side of the mounting groove 520, both sides of the mounting groove 520, and the stepped portions of the sound absorbing layer 500 located at both sides of the mounting groove 520.

A first separation groove 531 may be formed at both sides of the mounting groove 520 to form a first electrode layer 701 by dividing the electrode layer 700 (S140). The first separation groove 531 may be formed by a dicing process. When the dicing process is performed to form the first separation groove 531, the electrode layer 700 formed on both sides of the mounting groove 520 may be cut and removed. Therefore, the first electrode layer 701 may be formed at both sides of the mounting groove 520.

In this case, the first separation groove 531 may be cut to a depth greater than a depth of the mounting groove 520. In other words, the bottom side of the first separation groove 531 may be formed to be located below the bottom side of the mounting groove 520.

A piezoelectric body 600 may be stacked in the mounting groove 520 (S150). The piezoelectric body 600 may be stacked on the electrode layer 700 located on the bottom side of the mounting groove 520. Therefore, the electrode layer 700 on the bottom side of the mounting groove 520 and the first electrode 601 of the piezoelectric body 600 may be electrically connected.

A second separation groove 532 may be formed to form a second electrode layer 70 and a third electrode layer 703 in a state in which the piezoelectric body 600 is inserted into the mounting groove 520 (S160). The second separation groove 532 may be formed by the dicing process. The second separation groove 532 may be formed between the first center connection part 551 and the side connection part 560 or between the second center connection part 552 and the side connection part 560.

The second separation groove 532 may be formed by cutting the electrode layer 700 on the bottom side of the mounting groove 520 and the piezoelectric body 600 on the electrode layer 700. Due to the second separation groove 532, the electrode layer 700 may be divided into the second electrode layer 702 and the third electrode layer 703 and the piezoelectric body 600 may be divided into the side piezoelectric body 600b and the center piezoelectric body 600a. Accordingly, the side piezoelectric body 600b electrically connected to the second electrode layer 702 and the center piezoelectric body 600a electrically connected to the center connection parts 551 and 552 may be formed.

A sound matching layer 800 may be provided (S170). The sound matching layer 800 may be stacked on the piezoelectric body 600. The second electrode 602 of the piezoelectric body 600 and a front side of the first electrode layer 701 may be electrically connected to an electrode part 810 of the sound matching layer 800. Because a rear side of the first electrode layer 701 is electrically connected to the electrode 570a of the ground connection part 570, the piezoelectric body 600 may be electrically connected to the electrode 570a of the ground connection part 570 through the first electrode layer 701, the electrode part 810 and the second electrode 602 that are electrically connected to one another.

The piezoelectric body 600 may be divided into a plurality of columns C by kerfs 540 formed by the dicing process (S180). The dicing process for forming the kerfs 540 may be performed to a depth for reliable separation of the first electrode layer 701, the second electrode layer 702, the third electrode layer 703, and the electrode part 810.

The dicing process for forming the kerfs 540 may be performed after the stacking of the sound matching layer 800 but is not limited thereto and may be performed before the stacking of the sound matching layer 800.

The piezoelectric body 600 may be divided into the plurality of columns C, which are spaced a certain distance from each other, by the dicing process of forming the kerfs 540, and the electrode layer 700 in each of the plurality of columns C may be electrically disconnected from the electrode layer 700 in another adjacent column C.

The operations of the method of manufacturing the ultrasonic probe 100 need not necessarily be performed in the order described above, and may be performed in a different order or at the same time.

FIG. 16 is a flowchart of another example of a method of manufacturing the ultrasonic probe of FIG. 2. FIG. 17 is a diagram of a state in which a third separation groove is formed by the method of FIG. 10. Description of parts that have already been described will be omitted.

According to the method of manufacturing the ultrasonic probe 100 according to the flowchart of FIG. 16, a second separation groove 532 may be formed to form a second electrode layer 702 and a third electrode layer 703 after formation of a first separation groove 531 (S250).

As shown in FIG. 17, a third separation groove 610 corresponding to the second separation groove 532 may be formed in the piezoelectric body 600 (S260). When the piezoelectric body 600 is stacked on the second electrode layer 702 and the third electrode layer 703, the third separation groove 610 in the piezoelectric body 600 may face the second separation groove 532.

The piezoelectric body 600 and sound matching layer 800 may be provided (S270). The third separation groove 610 may be formed in the piezoelectric body 600. The piezoelectric body 600 may be stacked in a mounting groove 520, and the sound matching layer 800 may be stacked on the mounting groove 520. The piezoelectric body 600 and the sound matching layer 800 may be stacked at the same time.

Although the technical idea of the present disclosure has been described above with certain embodiments, the scope of the present disclosure is not limited thereto. It should be understood that various embodiments in which modifications or changes may be made by those of ordinary skill in the technical field to which the present disclosure pertains without departing from the technical idea of the present disclosure defined in the claims fall within the scope of the present disclosure.

The invention claimed is:

1. An ultrasonic probe comprising:
a plurality of sound absorbing bodies configured to form a sound absorbing layer;
at least one ground connection part joined between the plurality of sound absorbing bodies;
at least one center connection part joined between the plurality of sound absorbing bodies and including an electrode;
a plurality of side connection parts joined between the plurality of sound absorbing bodies and disposed further outward than the at least one center connection part, the plurality of side connection parts each including an electrode; and
a plurality of piezoelectric bodies disposed in front of the sound absorbing layer to be electrically connected to the at least one ground connection part, the at least one center connection part, and the plurality of side connection parts,
wherein the at least one center connection part comprises:
a first center connection part; and
a second center connection part including a plurality of electrodes formed not to face a plurality of electrodes of the first center connection part, the second center connection part being disposed apart from the first center connection part,
wherein the plurality of side connection parts comprise:
a first side connection part; and
a second side connection part including a plurality of electrodes corresponding to an array of a plurality of electrodes of the first side connection part,
wherein each of the plurality of electrodes of the first side connection part is electrically connected to each of the plurality of electrodes of the second side connection part, such that the first side connection part and the second side connection part simultaneously transmit signals,
wherein the plurality of electrodes of the first side connection part and the plurality of electrodes of the second side connection part are electrically separated from the plurality of electrodes of the first center part, or the plurality of electrodes of the first side connection part and the plurality of electrodes of the second side connection part are electrically separated from the plurality of electrodes of the second center connection part, such that the first center connection part or the second center connection part is configured to transmit signals independently of the first side connection part and the second side connection part.

2. The ultrasonic probe of claim 1, wherein a plurality of electrode layers are disposed on a surface of the sound absorbing layer.

3. The ultrasonic probe of claim 2, wherein the plurality of electrode layers comprise:
at least one first electrode layer electrically connected to the at least one ground connection part;
a plurality of second electrode layers electrically connected to the plurality of side connection parts; and
at least one third electrode layer electrically connected to the at least one center connection part.

4. The ultrasonic probe of claim 3, wherein the at least one first electrode layer, the plurality of second electrode layers, and the at least one third electrode layer are spaced apart from one another, and
the plurality of second electrode layers and the at least one third electrode layer are electrically connected to the plurality of piezoelectric bodies below the plurality of piezoelectric bodies.

5. The ultrasonic probe of claim 3, wherein a mounting groove is disposed in the sound absorbing layer, and the plurality of piezoelectric bodies are inserted into the mounting groove.

6. The ultrasonic probe of claim 5, wherein the plurality of second electrode layers and the at least one third electrode layer are disposed on a bottom side of the mounting groove.

7. The ultrasonic probe of claim 6, wherein the mounting groove comprises:
a first separation groove disposed on opposite sides of the mounting groove to separate the at least one first electrode layer and the plurality of second electrode layers from each other; and
a second separation groove disposed on the bottom side of the mounting groove to separate the plurality of second electrode layers and the at least one third electrode layer from each other.

8. The ultrasonic probe of claim 7, wherein a bottom side of the first separation groove and a bottom side of the second separation groove are located below the plurality of second electrode layers and the at least one third electrode layer.

9. The ultrasonic probe of claim 1, wherein a first side connection part of the plurality of side connection parts is disposed between the first center connection part and the at least one ground connection part, which is adjacent to the first center connection part, and a second side connection part of the plurality of side connection parts is disposed between the second center connection part and the at least one ground connection part, which is adjacent to the second center connection part.

10. The ultrasonic probe of claim 9, wherein piezoelectric bodies among the plurality of piezoelectric bodies electrically connected to the first center connection part and the second center connection part and piezoelectric bodies among the plurality of piezoelectric bodies electrically connected to the plurality of side connection parts are spaced apart from each other.

11. The ultrasonic probe of claim 1, wherein the plurality of electrodes of the first center connection part and the plurality of electrodes of the second center connection part are misaligned in a lateral direction.

* * * * *